US010688174B2

(12) United States Patent
Richardson et al.

(10) Patent No.: US 10,688,174 B2
(45) Date of Patent: Jun. 23, 2020

(54) METHOD OF CONFERRING A PROTECTIVE IMMUNE RESPONSE TO NOROVIRUS

(71) Applicant: Takeda Vaccines, Inc., Cambridge, MA (US)

(72) Inventors: Charles Richardson, Cambridge, MA (US); Thomas S. Vedvick, Cambridge, MA (US); Thomas R. Foubert, Cambridge, MA (US); William Tino, Cambridge, MA (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 16/429,580

(22) Filed: Jun. 3, 2019

(65) Prior Publication Data

US 2019/0381164 A1    Dec. 19, 2019

Related U.S. Application Data

(63) Continuation of application No. 16/155,120, filed on Oct. 9, 2018, now abandoned, which is a continuation of application No. 12/678,813, filed as application No. PCT/US2008/076763 on Sep. 18, 2008, now Pat. No. 10,130,696.

(60) Provisional application No. 60/986,826, filed on Nov. 9, 2007, provisional application No. 60/973,389, filed on Sep. 18, 2007.

(51) Int. Cl.
| | |
|---|---|
| *A61K 39/12* | (2006.01) |
| *A61K 39/00* | (2006.01) |
| *A61K 39/125* | (2006.01) |
| *C12N 7/00* | (2006.01) |
| *A61K 39/39* | (2006.01) |

(52) U.S. Cl.
CPC ............... *A61K 39/12* (2013.01); *C12N 7/00* (2013.01); *A61K 2039/5258* (2013.01); *A61K 2039/543* (2013.01); *A61K 2039/55572* (2013.01); *A61K 2039/55583* (2013.01); *C12N 2770/16023* (2013.01); *C12N 2770/16034* (2013.01)

(58) Field of Classification Search
CPC ............ A61K 39/12; A61K 2039/5258; C12N 2770/16034; C12N 7/00; C12N 2770/16023
See application file for complete search history.

(56) References Cited

U.S. PATENT DOCUMENTS

| | | | |
|---|---|---|---|
| 5,645,051 A | 7/1997 | Schultz et al. | |
| 5,861,241 A | 1/1999 | Herrmann et al. | |
| 5,953,727 A | 9/1999 | Maslyn et al. | |
| 6,165,502 A | 12/2000 | Oleske et al. | |
| 6,251,678 B1 | 6/2001 | Volkin et al. | |
| 6,391,318 B1 | 5/2002 | Ilium et al. | |
| 6,491,919 B2 | 12/2002 | Crane | |
| 6,572,862 B1 | 6/2003 | Estes et al. | |
| 6,602,697 B1 | 8/2003 | Cook, III | |
| 6,942,865 B2 | 9/2005 | Estes et al. | |
| 7,067,638 B1 | 6/2006 | Takeda et al. | |
| 7,481,997 B1 | 1/2009 | Hardy | |
| 7,527,801 B2 | 5/2009 | Coit et al. | |
| 7,955,603 B2 | 6/2011 | Richardson et al. | |
| 8,119,145 B2 | 2/2012 | Coit et al. | |
| 8,124,104 B2 | 2/2012 | Coit et al. | |
| 8,142,793 B2 | 3/2012 | Coit et al. | |
| 8,431,116 B2 | 4/2013 | Richardson et al. | |
| 8,841,120 B2 | 9/2014 | Richardson et al. | |
| 8,980,275 B2 | 3/2015 | Steadman et al. | |
| 9,272,028 B2 | 3/2016 | Richardson et al. | |
| 9,308,249 B2 | 4/2016 | Richardson et al. | |
| 9,518,096 B2 | 12/2016 | Richardson et al. | |
| 9,801,934 B2 | 10/2017 | Richardson et al. | |
| 9,821,049 B2 | 11/2017 | Richardson et al. | |
| 9,861,691 B2 | 1/2018 | Richardson et al. | |
| 9,867,876 B2 | 1/2018 | Richardson et al. | |
| 10,010,599 B2 | 7/2018 | Richardson et al. | |
| 10,130,696 B2 | 11/2018 | Richardson et al. | |
| 10,167,320 B2 | 1/2019 | Taylor | |
| 2004/0063188 A1 | 4/2004 | Robinson et al. | |
| 2004/0265377 A1 | 12/2004 | Seager | |
| 2005/0152911 A1 | 7/2005 | Hardy | |
| 2005/0154053 A1 | 7/2005 | Rhijn et al. | |
| 2005/0155113 A1 | 7/2005 | Hamilton et al. | |
| 2005/0215501 A1 | 9/2005 | Lipford et al. | |
| 2005/0260225 A1 | 11/2005 | Goldberg et al. | |
| 2007/0207526 A1* | 9/2007 | Coit ...................... | A61K 39/12 435/91.1 |
| 2008/0299152 A1 | 12/2008 | Richardson et al. | |
| 2010/0150961 A1 | 6/2010 | Vedvick et al. | |
| 2010/0266636 A1 | 10/2010 | Richardson et al. | |
| 2011/0070260 A1 | 3/2011 | Baric et al. | |
| 2011/0182975 A1 | 7/2011 | Richardson et al. | |
| 2011/0195113 A1 | 8/2011 | Richardson et al. | |
| 2012/0093861 A1 | 4/2012 | Richardson et al. | |
| 2012/0156243 A1 | 6/2012 | Richardson et al. | |
| 2013/0273102 A1 | 10/2013 | Richardson et al. | |
| 2013/0273105 A1 | 10/2013 | Richardson et al. | |
| 2013/0273147 A1 | 10/2013 | Richardson et al. | |
| 2013/0273148 A1 | 10/2013 | Richardson et al. | |

(Continued)

FOREIGN PATENT DOCUMENTS

| | | |
|---|---|---|
| EP | 1186890 A1 | 3/2002 |
| EP | 2360175 A2 | 8/2011 |

(Continued)

OTHER PUBLICATIONS

Allen et al., "Analysis of Amino Acid Variation in the P2 Domain of the GII-4 Norovirus VP1 Protein Reveals Putative Variant-Specific Epitopes," PLOS One, vol. 3: e1485, 2008.

(Continued)

*Primary Examiner* — Barry A Chestnut
(74) *Attorney, Agent, or Firm* — Cooley LLP

(57) ABSTRACT

The present invention relates to vaccine compositions comprising Norovirus antigens and adjuvants, in particular, mixtures of monovalent VLPs and mixtures of multivalent VLPs, and to methods of conferring protective immunity to Norovirus infections in a human subject.

20 Claims, 3 Drawing Sheets

(56) References Cited

U.S. PATENT DOCUMENTS

| | | | |
|---|---|---|---|
| 2014/0286994 | A1 | 9/2014 | Richardson et al. |
| 2015/0023995 | A1 | 1/2015 | Richardson et al. |
| 2016/0000899 | A1 | 1/2016 | Richardson et al. |
| 2016/0008455 | A1 | 1/2016 | Richardson et al. |
| 2018/0185468 | A1 | 7/2018 | Richardson et al. |
| 2019/0125853 | A1 | 5/2019 | Richardson et al. |

FOREIGN PATENT DOCUMENTS

| | | | |
|---|---|---|---|
| JP | 10-500847 | A | 1/1998 |
| JP | 2002-508748 | A | 3/2002 |
| JP | 2002-536340 | A | 10/2002 |
| JP | 2005-200420 | A | 7/2005 |
| JP | 2005-524674 | A | 8/2005 |
| JP | 2005-525415 | A | 8/2005 |
| JP | 2005-538939 | A | 12/2005 |
| JP | 2006-502979 | A | 1/2006 |
| JP | 2006-507800 | A | 3/2006 |
| JP | 2006-516638 | A | 7/2006 |
| JP | 2006-518748 | A | 8/2006 |
| JP | 2007-145775 | A | 6/2007 |
| JP | 2007-537137 | A | 12/2007 |
| JP | 2008-511556 | A | 4/2008 |
| JP | 2008-526870 | A | 7/2008 |
| JP | 2009-516529 | A | 4/2009 |
| JP | 2010-505766 | A | 2/2010 |
| JP | 2011-506264 | A | 3/2011 |
| JP | 5476544 | B | 4/2014 |
| WO | WO 1992/016543 | A1 | 10/1992 |
| WO | WO 1993/021325 | A1 | 10/1993 |
| WO | WO 1998/050071 | A1 | 11/1998 |
| WO | WO 2000/035479 | A1 | 6/2000 |
| WO | WO 2000/079280 | A1 | 12/2000 |
| WO | WO 2003/077942 | A2 | 9/2003 |
| WO | WO 2003/078455 | A2 | 9/2003 |
| WO | WO 2005/020889 | A2 | 3/2005 |
| WO | WO 2005/030806 | A2 | 4/2005 |
| WO | WO 2005/032457 | A2 | 4/2005 |
| WO | WO 2005/060966 | A1 | 7/2005 |
| WO | WO 2006/044857 | A2 | 4/2006 |
| WO | WO 2006/067632 | A2 | 6/2006 |
| WO | WO 2006/074303 | A2 | 7/2006 |
| WO | WO 2006/086188 | A2 | 8/2006 |
| WO | WO 2006/091517 | A2 | 8/2006 |
| WO | WO 2006/097530 | A2 | 9/2006 |
| WO | WO 2006/136566 | A1 | 12/2006 |
| WO | WO 2007/053188 | A2 | 5/2007 |
| WO | WO 2007/081447 | A2 | 7/2007 |
| WO | WO 2008/042789 | A1 | 4/2008 |
| WO | WO 2009/039229 | A2 | 3/2009 |
| WO | WO 2010/017542 | A1 | 2/2010 |
| WO | WO 2010/084298 | A1 | 7/2010 |
| WO | WO 2010/092476 | A1 | 8/2010 |
| WO | WO 2011/150249 | A1 | 12/2011 |
| WO | WO 2013/009849 | A1 | 1/2013 |

OTHER PUBLICATIONS

Ando et al., "Genetic Classification of 'Norwalk-like Viruses,'" The Journal of Infectious Diseases, vol. 181(Suppl 2): S336-S348, 2000.
Ausar et al., "Conformational stability and disassembly of norwalk virus like particles: effect of pH and temperature,"J. Biol. Chem., vol. 281: 19478-19488, 2006.
Baldrick et al., Safety evaluation of monophosphoryl lipid A (MPL): an immunostimulatory adjuvant. Regulatory Toxicology and Pharmacology 2002; vol. 35:398-413.
Baldridge et al., "Taking a Toll on human disease: Toll-like receptor 4 agonists as vaccine adjuvants and monotherapeutic agents," Exp. Opin. Biol. Ther. 4(7):1129-1138 (2004).
Baldridge et al., Monophosphoryl lipid A enhances mucosal and systemic immunity to vaccine antigens following intranasal administration. Vaccine 2000; vol. 18:2416-2425.

Ball et al., "Recombinant Norwalk virus-like particles as an oral vaccine." Archives of Virology (1996); 12: 243-249.
Ball et al., Oral Immunization with Recombinant Norwalk Virus-Like Particles Induces a Systemic and Mucosal Immune Response in Mice. Journal of Virology 1998; vol. 72(2): 1345-1353.
Ball et al., Recombinant Norwalk virus-like particles given orally to volunteers: phase I study. Gastroenterology 1999; vol. 117:40-48.
Baric et al., "Expression and Self-Assembly of Norwalk Virus Capsid Protein from Venezuelan Equine Encephalitis Virus Replicons," J. Virol. 76(6):3023-3030 (2002).
Bertolotti-Ciarlet et al., "Structural Requirements for the Assembly of Norwalk Virus-Like Particles," J. Virol. 76(8):4044-4055 (2002).
Bok et al., "Chimpanzees as an animal model for human norovirus infection and vaccine development," Proc. Natl. Acad. Sci. USA 108(1):325-330 (2011).
Bok, et al., "Evolutionary Dynamics of GII.4 Noroviruses over a 34-Year Period." Journal of Virology (2009); 83 (22): 11890-11901.
Broadbent and Subbarao, "Influenza virus vaccines: lessons from the 2009 H1N1 pandemic," Curr. Opin. Virol. 1:254-262 (2011).
Bull et al., "Emergence of a New Norovirus Genotype II.4 Variant Associated with Global Outbreaks of Gastroenteritis," Journal of Clinical Microbiology, vol. 44: 327-333, 2006.
Cachia et al., "The use of synthetic peptides in the design of a consensus sequence vaccine for Pseudomonas aeruginosa," J. Pept. Res. 52(4):289-299 (1998).
Cannon, et al., "Herd Immunity to GII.4 Noroviruses Is Supported by Outbreak Patient Sera." Journal of Virology (2009); 83 (11): 5363-5374.
Cao et al., "Structural Basis for the Recognition of Blood Group Trisaccharides by Norovirus," J. Virol. 81(11):5949-5957 (2007).
Carpenter et al., Rational design of stable lyophilized protein formulations: some practical advice, Pharmaceutical Research, vol. 14: 969-975, 1997.
Chachu, Karen A., et al. "Immune mechanisms responsible for vaccination against and clearance of mucosal and lymphatic norovirus infection." PLoS Pathog (2008); 4.12: e1000236, 13 pages.
Cheetham et al., "Binding patterns of human norovirus-like particles to buccal and intestinal tissues of gnotobiotic pigs in relation to A/H histo-blood group antigen expression," Journal of Virology, vol. 81: 3535-3544, 2007.
Chen et al., "X-ray structure of a native calicivirus: Structural insights into antigenic diversity and host specificity," Proc. Natl Acad. Sci. USA 103(21):8048-8053 (2006).
Childers et al., "Adjuvant activity of monophosphoryl lipid A for nasal and oral immunization with soluble or liposome-associated antigen," Infection and Immunity, vol. 68: 5509-5516, 2000.
Clark and Offit, "Vaccines for rotavirus gastroenteritis universally needed for infants." Pediatric Annals (2004); 33(8): 537-543.
Communication from the European Patent Office dated Sep. 4, 2018 in Opposition Proceedings against European Patent No. EP 2601970 (Application No. EP 13157573.0), with Response to Opposition Division's Preliminary Opinion, filed Aug. 30, 2018, 17 pages.
Cuellar et al., "Size and mechanical stability of norovirus capsids depend on pH: a nanoindentation study," J. Gen. Virol. 91:2449-2456 (2010).
Da Silva et al., "Adsorption and Aggregation Properties of Norovirus GI and GII Virus-like Particles Demonstrate Differing Responses to Solution Chemistry," Environ. Sci. Technol. 45(2):520-526 (2011).
Dagan et al., "Reduced Response to Multiple Vaccines Sharing Common Protein Epitopes That Are Administered Simultaneously to Infants," Infect. Immun. 66(5):2093-2098 (1998).
Davis and Illum, Absorption enhancers for nasal drug delivery. Clinical Pharmacokinetics 2003; vol. 42:1107-1128.
Document 4 of the Handouts of the meeting on food poisoning held on Aug. 17, 2007, Food Sanitation Council, Pharmaceutical Affairs and Food Sanitation Council, Ministry of Health, Labour and Welfare, and English Summary, 21 pages.
El-Kamary, S.S., et al., "Adjuvanted Intranasal Norwalk Virus-Like Particle Vaccine Elicits Antibodies and Antibody-Secreting Cells That Express Homing Receptors for Mucosal and Peripheral Lymphoid Tissues." J. Infect Dis. (Dec. 2010); 202(11): 1649-1658.

(56) References Cited

OTHER PUBLICATIONS

Estes et al., "Norwalk Virus Vaccines: Challenges and Progress." The Journal of Infectious Disease 2000; vol. 181(Suppl 2): S367-373.
Extended European Search Report for European Patent Application No. 18158843.5, dated Jun. 15, 2018, 10 pages.
Extended European Search Report, EP appl. No. 13157572.2, 9 pages (dated Jul. 23, 2013).
Extended European Search Report, EP appl. No. 13157573.0, 6 pages (dated Apr. 5, 2013).
Extended European Search Report, EP appl. No. 13173005.3, 5 pages (dated Jul. 16, 2013).
Extended European Search Report, EP appln. No. 07853688.5, 9 pages (dated Sep. 22, 2010).
Extended European Search Report, EP Appln. No. 17199372.8, dated Jan. 23, 2018, 10 pages.
Fankhauser et al., "Molecular Epidemiology of "Norwalk-like viruses" in Outbreaks of Gastroenteritis in the United States," J. Infect. Dis. 178(6):1571-1578 (1998).
Foubert et al., "Preclinical Development of a Broad Spectrum Norovirus Vaccine," AAPS National Biotechnology Conference, http://abstracts.aapspharmaceutica.com/ExpoNBC09/CC/forms/attendee/index.aspx?content=sessionInfo&sessionId=150 (2009).
Frey et al., "Interference of Antibody Production to Hepatitis B Surface Antigen in a Combination Hepatitis A/Hepatitis B Vaccine," J. Infect. Dis. 180:2018-2022 (1999).
Giannini et al., "Enhanced humoral and memory B cellular immunity using HPV16/18 L1 VLP vaccine formulated with the MPL/aluminium salt combination (AS04) compared to aluminium salt only," Vaccine 24:5937-5949 (2006).
Glass, R.I., et al. "Norovirus gastroenteritis." New England Journal of Medicine (2009); 361.18: 1776-1785.
Gray et al., Detection of immunoglobulin M (IgM), IgA, and IgG Norwalk virus-specific antibodies by indirect enzyme-linked immunosorbent assay with baculovirus-expressed Norwalk virus capsid antigen in adult volunteers challenged with Norwalk virus. Journal of Clinical Microbiology 1994; vol. 32:3059-3063.
Guerrero et al., Recombinant Norwalk Virus-Like Particles Administered Intranasally to Mice Induce Systemic and Mucosal (Fecal and Vaginal) Immune Responses. Journal of Virology 2001; vol. 75:9713-9722.
Guy et al., "Evaluation of Interferences between Dengue Vaccine Serotypes in a Monkey Model,"Am. J. Trop. Med. Hyg. 80(2):302-311 (2009).
Han et al., "Thermosensitive and mucoadhesive delivery systems of mucosal vaccines," Methods, vol. 38:106-111, 2006.
Han et al., Immune responses to bovine norovirus-like particles with various adjuvants and analysis of protection in gnotobiotic calves. Vaccine 2006; vol. 24:317-326.
Hansman et al., Genetic and antigenic diversity among Noroviruses. Journal of General Virology 2006; vol. 87: 909-919.
Hardy, Michele E., "Norovirus protein structure and function", FEMS Microbiology (2005); 253: 1-8.
Harrington et al., "Systemic, Mucosal, and Heterotypic Immune Induction in Mice Inoculated with Venezuelan Equine Encephalitis Replicons Expressing Norwalk Virus-Like Particles," J. Virol. 76(2):730-742 (2002).
Herbst-Kralovetz et al., "Norwalk virus-like particles as vaccines," Exp. Rev. Vaccines 9(3):299-307 (2010).
Huang et al., "Noroviruses Bind to Human ABO, Lewis, and Secretor Histo-Blood Group Antigens: Identification of 4 Distinct Strain-Specific Patterns," J. Infect. Dis. 188(1):19-31 (2003).
Hutson et al., "Norwalk Virus-Like Particle Hemagglutination by Binding to H Histo-Blood Group Antigens," J. Virol. 77(1):405-415 (2003).
Hutson et al., Norovirus disease: changing epidemiology and host susceptibility factors. TRENDS in Microbiology 2004; vol. 12(6):279-287.
Illum et al., Chitosan as a novel nasal delivery system for peptide drugs. Pharmaceutical Research 1994.; vol. 11:1186-1189.
Illum et al., Chitosan as a novel nasal delivery system for vaccines. Advanced Drug Delivery Reviews 2001; vol. 51:81-96.
Illum et al., Nasal drug delivery—possibilities, problems and solutions. Journal of Controlled Release 2003; vol. 87:187-198.
International Preliminary Report on Patentability, 6 pages, PCT appl. No. PCT/US2008/076763 dated Mar. 24, 2010.
International Preliminary Report on Patentability, 7 pages, PCT appl. No. PCT/US2012/046222, dated Jan. 14, 2014.
International Preliminary Report on Patentability, 8 pages, PCT appl. No. PCT/US2009/053249 dated Feb. 8, 2011.
International Preliminary Report on Patentability, PCT appl. No. PCT/US2007/079929 dated Mar. 31, 2009.
International Search Report, 2 pages, PCT appl. No. PCT/US2007/079929 (dated Mar. 11, 2008).
International Search Report, 3 pages, PCT appl. No. PCT/US2008/076763 (dated Jul. 15, 2009).
International Search Report, 3 pages, PCT appl. No. PCT/US2009/053249 (dated Dec. 14, 2009).
International Search Report, 3 pages, PCT appl. No. PCT/US2012/046222 (dated Oct. 2, 2012).
Jaimes et al., "Maturation and Trafficking Markers on Rotavirus-Specific B Cells during Acute Infection and Convalescence in Children," J. Virol 78:10967-10976 (2004).
Jiang et al., "Norwalk virus genome cloning and characterization," Science 250:1580-1583 (1990).
Jiang et al., "Expression, Self-Assembly, and Antigenicity of the Norwalk Virus Capsid Protein," J. Virol. 66(11):6527-6532 (1992).
Johnson et al., Multiple Challenge Study of Host Susceptibility to Norwalk Gastroenteritis in U.S. Adults. The Journal of Infectious Disease 1990; vol. 161: 18-21.
Kamata et al., "Increased Frequency of Surface IgA-Positive Plasma Cells in the Intestinal Lamina Propia and Decreased IgA Excretion in Hyper IgA (HIGA) Mice, a Murine Model of IgA Nephropathy with Hyperserum IgA," J. Immunol. 165:1387-1394 (2000).
Kawana et al., "A surface immunodeterminant of human papillomavirus type 16 minor capsid protein L2." Virology (1998); 245.2: 353-359.
Kitamoto et al., "Cross-Reactivity among Several Recombinant Calicivirus Virus-Like Particles (VLPs) with Monoclonal Antibodies Obtained from Mice Immunized Orally with One Type of VLP." J. Clin. Microbiol. (2002); 40(7): 2459-2465.
Larke et al., "Combined single-clade candidate HIV-1 vaccines induce T cell responses limited multiple forms of in vivo immune interference," Eur. J. Immunol. 37:566-577 (2007).
Lew et al., "Molecular Characterization and Expression of the Capsid Protein of a Norwalk-like Virus Recovered from a Desert Shield Troop with Gastroenteritis," Virol. 319-325 (1994).
Ligocyte Pharmaceuticals, "Ligocyte Pharmaceuticals initiates U.S. clinical trial of norovirus vaccine," http://www.ligocyte.com/news/documents/LIGOCYTE-PHARMACEUTICALS-4-3-2007.pdf, Apr. 3, 2007, 2 pages.
Lin, S.W., et al., "Intramuscular rather than oral administration of replication-defective adenoviral vaccine vector induces specific CD8+ T-cell responses in the gut." Vaccine (2007); 25(12): 2187-2193.
Lindell et al., "Molecular Epidemiology of Norovirus Infections in Stockholm, Sweden, during the Years 2000 to 2003: Association of the GGIIb Genetic Cluster with Infection in Children," Journal of Clinical Microbiology, vol. 43: 1086-1092, 2005.
Lindesmith et al., Cellular and humoral immunity following Snow Mountain virus challenge. Journal of Virology 2005; vol. 79(5): 2900-2909.
Lindesmith et al., Human susceptibility and resistance to Norwalk infection. Nature Medicine 2003; vol. 9(5): 548-553.
Lindesmith et al., "Mechanisms of GII.4 Norovirus Persistence in Human Populations," PLOS One, vol. 5: e31, 2008.
Lindesmith, et al., "Mechanisms of GII.4 Norovirus Persistence in Human Populations." PLoS Medicine (2008); 5 (2): 269-290.
Liu, Guangliang, et al. "Primary high-dose murine norovirus 1 infection fails to protect from secondary challenge with homologous virus." Journal of Virology (2009); 83.13: 6963-6968.

(56) References Cited

OTHER PUBLICATIONS

Liu, X.S., et al., "Mucosal Immunisation with Papillomavirus Virus-like Particles Elicits Systemic and Mucosal Immunity in Mice." Virology (Dec. 1998); 252(1): 39-45.
Lobue et al., "Alphavirus adjuvanted norovirus-like particle vaccines: heterologous, humoral, and mucosal immune responses protect against murine norovirus challenge," J. Virol., vol. 83(7): 3212-3227, 2009.
Lobue et al., Multivalent Norovirus vaccines induce strong mucosal and systemic blocking antibodies against multiple strains. Vaccine 2006; vol. 24(24): 5220-5234.
Malcolmson and Embleton, "Dry powder formulations for pulmonary delivery," Pharmaceutical Science and Technology Today, vol. 1:394-398, 1998.
Martin et al., "Role of Innate Immune Factors in the Adjuvant Activity of Monophosphoryl Lipid A," Infect. Immun. 71(5):2498-2507 (2003).
Mason et al., "Expression of Norwalk virus capsid protein in transgenic tobacco and potato and its oral immunogenicity in mice," Proc. Natl Acad. Sci. USA 93(11):5335-5340 (1996).
Matsui et al., Immunity to Calicivirus infection. The Journal of Infectious Diseases 2000; vol. 181(S2): S331-335.
McBurney et al., "Developing Broadly Reactive HIV-1/AIDS Vaccines: A Review of Polyvalent and Centralized HIV-1 Vaccines," Curr. Pharm. Design 13(19):1957-1964 (2007).
Mead et al., Food Related Illness and Death in the U.S., Emerging Infectious Diseases 1999; vol. 5(5): 607-635.
Midthun and Kapikian. "Rotavirus vaccines: an overview." Clinical Microbiology Reviews (1996); 9(3): 423-434.
MMWR, 2011, Updated Norovirus Outbreak Management and Disease Prevention Guidelines, 20 pages. [https://www.cdc.gov/mmwr/preview/mmwrhtml/rr6003a1.htm] downloaded May 1, 2017.
Motomura, et al., "Divergent Evolution of Norovirus GII/4 by Genome Recombination from May 2006 to Feb. 2009 in Japan." Journal of Virology (2010); 84 (16): 8085-8097.
Motomura, et al., "Identification of Monomorphic and Divergent Haplotypes in the 2006-2007 Norovirus GII/4 Epidemic Population by Genomewide Tracing of Evolutionary History." Journal of Virology (2008); 82 (22): 11247-11262.
Muthumani et al., "Immunogenicity of novel consensus-based DNA vaccines against Chikungunya virus," Vaccine 26(40):5128-5134 (2008).
Nakagomi, Osamu, "[Commonly-discussed Infectious Diseases]", Norovirues infection: some new developments in its research. Modern Media (2004); vol. 50, No. 6, pp. 133-142 (with partial English translation), 11 pages.
Nakata, S., "Vaccine development for Norwalk Virus." Nippon Rinsho (2002); 60(6): 1222-1227 (with English Abstract and English translation), 12 pages.
Nicollier-Jamot et al., Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. Vaccine 2004; vol. 22:1079-1086.
Noel et al., Correlation of patient immune responses with genetically characterized small round-structured viruses involved in outbreaks of nonbacterial acute gastroenteritis in the United States, 1990 to 1995. Journal of Medical Virology 1997; vol. 53:372-383.
Notice of Opposition in European Patent No. EP 2601970 (Application No. EP 13157573.0), filed Jul. 21, 2017, 40 pages.
O'Hagan et al., "Recent developments in adjuvants for vaccines against infectious diseases," Biomol. Eng. 18(3):69-85 (2001).
Oliver, S. L., et al. "Genotype 1 and genotype 2 bovine noroviruses are antigenically distinct but share a cross-reactive epitope with human noroviruses." Journal of Clinical Microbiology (2006); 44.3: 992-998.
Parra and Green, "Sequential Gastroenteritis Episodes Caused by 2 Norovirus Genotypes," Emerg. Infect. Dis. 20(6):1016-1018 (2014).
Parra, et al., "Immunogenicity and specificity of norovirus Consensus GII.4 virus-like particles in monovalent and bivalent vaccine formulations." Vaccine (2012); 30 (24): 3580-3586.
Parra, et al., "Static and Evolving Norovirus Genotypes: Implications for Epidemiology and Immunity." PLoS Pathog. (2017); 13 (1): e1006136.
Parrino et al., Clinical immunity in acute gastroenteritis caused by Norwalk agent. New England Journal of Medicine 1977; vol. 297:86-89.
Partial European Search Report, 7 pages, EP appl. No. 13157572.2 (dated Apr. 5, 2013).
Pastrana et al., "Cross-neutralization of cutaneous and mucosal Papillomavirus types with anti-sera to the amino terminus of L2." Virology (2005); 337.2: 365-372.
Pelosi et al., "The Seroepidemiology of Genogroup 1 and Genogroup 2 Norwalk-Like Viruses in Italy," J. Med. Virol. 58:93-99 (1999).
Periwal et al., A Modified Cholera Holotoxin CT-E29H Enhances Systemic and Mucosal Immune Responses to Recombinant Norwalk Virus-like Particle Vaccine. Vaccine 2003; vol. 21:376-385.
Prasad et al., "Structural studies of recombinant norwalk capsids," J. Infect. Dis., vol. 181(s2), S317-S321, 2000.
Rasmussen et al., "In Multiple Myeloma Clonotypic CD38−/CD19+/CD27+ Memory B Cells Recirculate Through Bone Marrow, Peripheral Blood and Lymph Nodes," Leuk. Lymph. 45(7):1413-1417 (2004).
Reagan-Shaw et al., "Dose translation from animal to human studies revisited," FASEB J. 22:659-661 (2007).
Richardson et al., "Norovirus virus-like particle vaccines for the prevention of acute gastroenteritis," Expert Rev. Vaccines (2013); 12 (2):155-167.
Richardson et al., "Norovirus Vaccine Formulations," U.S. Appl. No. 12/816,495, filed Jun. 16, 2010.
Sato, "Survival strategies of human norovirus." Virus, official journal of the Japanese Society for Virology (2010); 60 (1): 21-32 (and English Abstract).
Sato, et al., "Evolutionary Constraints on the Norovirus Pandemic Variant GII.4_2006b over the Five-Year Persistence in Japan." Frontiers in Microbiology (2017); 8 (410): 1-9.
Sha et al., "Activation of Airway Epithelial Cells by Toll-Like Receptor Agonists," Am. J. Respir. Cell Mol. Biol. 31(3):358-364 (2004).
Siebenga et al., "Epochal Evolution of GGII.4 Norovirus Capsid Proteins from 1995 to 2006," Journal of Virology, vol. 81: 9932-9941, 2007.
Singh et al., "A preliminary evaluation of alternative adjuvants to alum using a range of established and new generation vaccine antigens," Vaccine 24(10):1680-1686 (2006).
Singh, et al., "A novel bioadhesive intranasal delivery system for inactivated influenza vaccines." Journal of Controlled Release (2001); 70: 267-276.
Song, Wei, et al., "Research Progress on Molecular Biology Feature of Noroviruses and its Subunit Vaccine." Journal of Agricultural Science and Technology (2010); 12(6): 43-48 (with English Abstract).
Souza et al., "A human norovirus-like particle adjuvanted with ISCOM or mLT induces cytokine and antibody responses and protection to the homologous GII.4 human norovirus in a gnotobiotic pig disease model," Vaccine, vol. 25: 8448-8459, 2007.
Supplementary European Search Report, 13 pages, EP appl. No. 08832560.0 (dated Apr. 5, 2012).
Supplementary European Search Report, 8 pages, EP appl. No. 09805653.4 (dated Dec. 2, 2011).
Supplementary European Search Report, EP appl. No. 12811916.1, 8 pages (dated Feb. 20, 2015).
Tacket et al., "Human immune responses to a novel norwalk virus vaccine delivered in transgenic potatoes.," J. Infect. Dis., vol. 182(1): 302-305, 2000.
Tacket et al., Humoral, mucosal, and cellular immune response to oral Norwalk virus-like particles in volunteers. Clinical Immunology 2003; vol. 108: 241-247.
Third-Party Submission Under 37 C.F.R. § 1.290, in connection with U.S. Appl. No. 15/836,030, filed Dec. 18, 2018, 22 pages.
Third Party Observation against EP Application No. 17199372.8, dated Mar. 8, 2019, 22 pages.

(56) References Cited

OTHER PUBLICATIONS

EPO Communication dated Mar. 14, 2019 regarding Third Party Observation against EP Application No. 17199372.8, dated Mar. 8, 2019, 1 page.
Ugwoke et al., "Nasal mucoadhesive drug delivery: Background, applications, trends and future perspectives," Advanced Drug Delivery Reviews, vol. 57: 1640-1665, 2005.
Van Der Lubben, et al., "Chitosan and its derivatives in mucosal drug and vaccine delivery." European Journal of Pharmaceutical Sciences (2001); 14: 201-207.
Wang et al., "Effective synthetic peptide vaccine for foot-and-mouth disease in swine," Vaccine 20(19-20):2603-2610 (2002).
Written Opinion of the International Searching Authority, 4 pages, PCT appl. No. PCT/US2007/079929 (dated Mar. 11, 2008).
Written Opinion of the International Searching Authority, 5 pages, PCT appl. No. PCT/US2008/076763 (dated Jul. 15, 2009).
Written Opinion of the International Searching Authority, 6 pages, PCT appl. No. PCT/US2012/046222 (dated Oct. 2, 2012).
Written Opinion of the International Searching Authority, 7 pages, PCT appl. No. PCT/US2009/053249 (dated Dec. 14, 2009).
Wyatt et al., Comparison of three agents of acute infectious nonbacterial gastroenteritis by cross-challenge in volunteers. Journal of Infectious. Diseases (1974); vol. 129: 709-714.
Xia et al., "Norovirus Capsid Protein Expressed in Yeast Forms Virus-like Particles and Stimulates Systemic and Mucosal Immunity in Mice Following an Oral Administration of Raw Yeast Extracts," J. Med Virol. 79:74-83 (2007).
Zhang et al., "Trivalent Human Papillomavirus (HPV) VLP vaccine covering HPV type 58 can elicit high level of humoral immunity but also induce immune interference among component types," Vaccine 28:3479-3487 (2010).
Zheng et al., "Norovirus classification and proposed strain nomenclature," Virology 346:312-323 (2006).

\* cited by examiner

METHOD OF CONFERRING A PROTECTIVE IMMUNE RESPONSE TO NOROVIRUS

CROSS-REFERENCE TO RELATED APPLICATIONS

This application is a continuation of U.S. patent application Ser. No. 16/155,120, filed Oct. 9, 2018, which is a continuation of U.S. patent application Ser. No. 12/678,813, filed Jul. 6, 2010 (now U.S. Pat. No. 10,130,696, issued Nov. 20, 2018), which is the U.S. national stage application of International Patent Application No. PCT/US2008/076763, filed Sep. 18, 2008, which claims the benefit of priority of U.S. Provisional Patent Application No. 60/973,389, filed Sep. 18, 2007, and U.S. Provisional Patent Application No. 60/986,826, filed Nov. 9, 2007, all of which are herein incorporated by reference in their entireties.

STATEMENT OF GOVERNMENT SUPPORT

This invention was made with Government support under W81XWH-05-C-0135 awarded by the U.S. Army. The Government has certain rights in this invention.

FIELD OF THE INVENTION

The invention is in the field of vaccines, particularly vaccines for Noroviruses. In addition, the invention relates to methods of preparing vaccine compositions and methods of inducing a protective immune response.

BACKGROUND OF THE INVENTION

Noroviruses are non-cultivatable human Caliciviruses that have emerged as the single most important cause of epidemic outbreaks of nonbacterial gastroenteritis (Glass et al., 2000; Hardy et al., 1999). The clinical significance of Noroviruses was under-appreciated prior to the development of sensitive molecular diagnostic assays. The cloning of the prototype genogroup I Norwalk virus (NV) genome and the production of virus-like particles (VLPs) from a recombinant Baculovirus expression system led to the development of assays that revealed widespread Norovirus infections (Jiang et al. 1990; 1992).

Noroviruses are single-stranded, positive sense RNA viruses that contain a non-segmented RNA genome. The viral genome encodes three open reading frames, of which the latter two specify the production of the major capsid protein and a minor structural protein, respectively (Glass et al. 2000). When expressed at high levels in eukaryotic expression systems, the capsid protein of NV, and certain other Noroviruses, self-assembles into VLPs that structurally mimic native Norovirus virions. When viewed by transmission electron microscopy, the VLPs are morphologically indistinguishable from infectious virions isolated from human stool samples.

Immune responses to Noroviruses are complex, and the correlates of protection are just now being elucidated. Human volunteer studies performed with native virus demonstrated that mucosally-derived memory immune responses provided short-term protection from infection and suggested that vaccine-mediated protection is feasible (Lindesmith et al. 2003; Parrino et al. 1997; Wyatt et al., 1974).

Although Norovirus cannot be cultivated in vitro, due to the availability of VLPs and their ability to be produced in large quantities, considerable progress has been made in defining the antigenic and structural topography of the Norovirus capsid. VLPs preserve the authentic confirmation of the viral capsid protein while lacking the infectious genetic material. Consequently, VLPs mimic the functional interactions of the virus with cellular receptors, thereby eliciting an appropriate host immune response while lacking the ability to reproduce or cause infection. In conjunction with the NIH, Baylor College of Medicine studied the humoral, mucosal and cellular immune responses to NV VLPs in human volunteers in an academic, investigator-sponsored Phase I clinical trial. Orally administered VLPs were safe and immunogenic in healthy adults (Ball et al. 1999; Tacket et al. 2003). At other academic centers, preclinical experiments in animal models have demonstrated enhancement of immune responses to VLPs when administered intranasally with bacterial exotoxin adjuvants (Guerrero et al. 2001; Nicollier-Jamot et al. 2004; Periwal et al. 2003; Souza et al. (2007) Vaccine, doi: 10.1016/j.vaccine.2007.09.040). However, no studies have reported being able to achieve protective immunity against Norovirus using any Norovirus vaccine.

SUMMARY OF THE INVENTION

The present invention provides methods of inducing protective immunity to a Norovirus infection in a subject, in particular a human subject, comprising administering a vaccine comprising at least one Norovirus antigen. In one embodiment, the antigen is a Norovirus virus-like particle (VLP). Vaccines used in the methods of the invention may further comprise one or more adjuvants. The Norovirus VLPs can be selected from genogroup I or genogroup II virus or a mixture thereof. In one embodiment, the vaccine comprises Norovirus VLPs in a concentration from about 0.01% to about 80% by weight. In another embodiment, the vaccine comprises dosages of Norovirus VLPs from about 1 µg to about 100 mg per dose.

In some embodiments, the vaccine further comprises a delivery agent, which functions to enhance antigen uptake, provide a depot effect, increase antigen retention time at the site of delivery, or enhance the immune response through relaxation of cellular tight junctions at the delivery site. The delivery agent can be a bioadhesive, preferably a mucoadhesive selected from the group consisting of deunatan sulfate, chondroitin, pectin, mucin, alginate, cross-linked derivatives of poly(acrylic acid), polyvinyl alcohol, polyvinyl pyrollidone, polysaccharides, hydroxypropyl methylcellulose, lectins, fimbrial proteins, and carboxymethylcellulose. Preferably, the mucoadhesive is a polysaccharide. More preferably, the mucoadhesive is chitosan, or a mixture containing chitosan, such as a chitosan salt or chitosan base.

In other embodiments, the vaccine comprises an adjuvant. The adjuvant may be selected from the group consisting of toll-like receptor (TLR) agonists, monophosphoryl lipid A (MPL®), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, endotoxins, for instance bacterial endotoxins and liposomes. Preferably, the adjuvant is a toll-like receptor (TLR) agonist. More preferably, the adjuvant is MPL®.

The methods of the present invention include administering Norovirus vaccines formulated as a liquid or a dry powder. Dry power formulations may contain an average particle size from about 10 to about 500 micrometers in diameter. Suitable routes for administering the vaccine include mucosal, intramuscular, intravenous, subcutaneous, intradermal, subdermal, or transdermal. In particular, the route of administration may be intramuscular or mucosal, with preferred routes of mucosal administration including intranasal, oral, or vaginal routes of administration. In another embodiment, the vaccine is formulated as a nasal spray, nasal drops, or dry powder, wherein the vaccine is administered by rapid deposition within the nasal passage from a device containing the vaccine held close to the nasal passageway. In another embodiment, the vaccine is administrated to one or both nostrils.

DETAILED DESCRIPTION OF THE INVENTION

Figure 1:
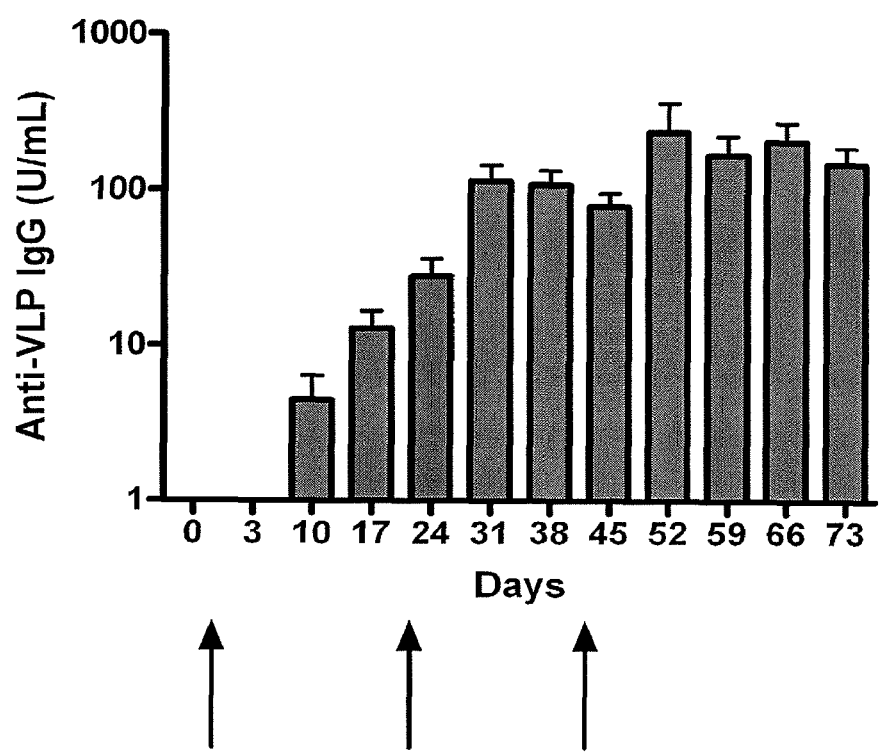
FIG. 1 shows that Norwalk Virus (NV)-specific IgG is elicited in rabbits immunized with dry powder VLPs. Rabbits were dosed 3 times, via the intranasal route of administration, on days 1, 22 and 43 (arrows) with 50 µg NV-VLP+50 µg MPL. Serum from each rabbit was tested for NV-VLP-specific IgG by ELISA on the days indicated. Only the VLP vaccinated rabbits had NV-VLP-specific IgG, whereas the untreated and placebo treatment groups had no detectable antigen-specific antibodies (data not shown). Arithmetic means of the responses are shown and expressed in U/mL (1 U~1 µg). Bars indicate the standard error of the mean.

The present invention relates to methods of eliciting a protective immunity to Norovirus infections in a subject. In particular, the present invention provides methods of administering a vaccine comprising Norovirus VLPs and at least one adjuvant to a human, wherein the vaccine confers protection from at least one symptom of Norovirus infection. Additionally or alternatively, the vaccine may further comprise at least one delivery agent.

Norovirus Antigens

The invention provides a composition comprising one or more Norovirus antigens. By "Norovirus," "Norovirus (NOR)," "norovirus," and grammatical equivalents herein, are meant members of the genus Norovirus of the family Caliciviridae. In some embodiments, a Norovirus can include a group of related, positive-sense single-stranded RNA, nonenveloped viruses that can be infectious to human or non-human mammalian species. In some embodiments, a Norovirus can cause acute gastroenteritis in humans. Noroviruses also can be referred to as small round structured viruses (SRSVs) having a defined surface structure or ragged edge when viewed by electron microscopy. Included within the Noroviruses are at least four genogroups (GI-IV) defined by nucleic acid and amino acid sequences, which comprise 15 genetic clusters. The major genogroups are GI and GII. GIII and GIV are proposed but generally accepted. Representative of GIII is the bovine, Jena strain. GIV contains one virus, Alphatron, at this time. For a further description of Noroviruses see Vinje et al. J. Clin. Micro. 41:1423-1433 (2003). By "Norovirus" also herein is meant recombinant Norovirus virus-like particles (rNOR VLPs). In some embodiments, recombinant expression of at least the Norovirus capsid protein encoded by ORF2 in cells, e.g., from a baculovirus vector in Sf9 cells, can result in spontaneous self-assembly of the capsid protein into VLPs. In some embodiments, recombinant expression of at least the Norovirus proteins encoded by ORF1 and ORF2 in cells, e.g., from a baculovirus vector in Sf9 cells, can result in spontaneous self-assembly of the capsid protein into VLPs. VLPs are structurally similar to Noroviruses but lack the viral RNA genome and therefore are not infectious. Accordingly, "Norovirus" includes virions that can be infectious or non-infectious particles, which include defective particles.

Non-limiting examples of Noroviruses include Norwalk virus (NV, GenBank M87661, VP1 sequence NP_056821), Southampton virus (SHV, GenBank L07418), Desert Shield virus (DSV, GenBank U04469), Hesse virus (HSV), Chiba virus (CHV, GenBank AB042808), Hawaii virus (HV, GenBank U0761), Snow Mountain virus (SMV, GenBank U70059), Toronto virus (TV, Leite et al., Arch. Virol. 141: 865-875), Bristol virus (BV), Jena virus (JV, GenBank AJ011099AJ01099), Maryland virus (MV, GenBank AY032605), Seto (Aichi) virus (SV, GenBank AB031013), Camberwell (CV, GenBank AF145896), Lordsdale virus (LV, GenBank X86557), Grimsby virus (GrV, GenBank AJ004864), Mexico virus (MXV, GenBank U22498), Boxer (GenBank AF538679), C59 (GenBank AF435807), VA115 (GenBank AY038598), BUDS (GenBank AY660568), Houston virus (HoV, GenBank EU310927, MOH (GenBank AF397156), Paris Island (PiV, GenBank AY652979), VA387 (GenBank AY038600), VA207 (GenBank AY038599), and Operation Iraqi Freedom (OIF, GenBank AY675554). The nucleic acid and corresponding amino acid sequences of each are all incorporated by reference in their entirety. In some embodiments, a cryptogram can be used for identification purposes and is organized: host species from which the virus was isolated/genus abbreviation/species abbreviation/strain name/year of occurrence/country of origin. (Green et al., Human Caliciviruses, in Fields Virology Vol. 1 841-874 (Knipe and Howley, editors-in-chief, 4th ed., Lippincott Williams & Wilkins 2001)). Norwalk virus, Snow Mountain virus, and Houston virus are preferred in some embodiments.

The Norovirus antigen may be in the form of peptides, proteins, or virus-like particles (VLPs). In a preferred embodiment, the Norovirus antigen comprises VLPs. As used herein, "virus-like particle(s) or VLPs" refer to a virus-like particle(s), fragment(s), aggregates, or portion(s) thereof produced from the capsid protein coding sequence of Norovirus and comprising antigenic characteristic(s) similar to those of infectious Norovirus particles. Norovirus antigens may also be in the form of capsid monomers, capsid multimers, protein or peptide fragments of VLPs, or aggregates or mixtures thereof. The Norovirus antigenic proteins or peptides may also be in a denatured form, produced using methods known in the art.

The VLPs of the present invention can be formed from either the full length Norovirus capsid protein such as VP1 and/or VP2 proteins or certain VP1 or VP2 derivatives using standard methods in the art. Alternatively, the capsid protein used to form the VLP is a truncated capsid protein. In some embodiments, for example, at least one of the VLPs comprises a truncated VP1 protein. In other embodiments, all the VLPs comprise truncated VP1 proteins. The truncation may be an N- or C-terminal truncation. Truncated capsid proteins are suitably functional capsid protein derivatives. Functional capsid protein derivatives are capable of raising an immune response (if necessary, when suitably adjuvanted) in the same way as the immune response is raised by a VLP consisting of the full length capsid protein.

VLPs may contain major VP1 proteins and/or minor VP2 proteins. Preferably each VLP contains VP1 and/or VP2 protein from only one Norovirus genogroup giving rise to a monovalent VLP. As used herein, the term "monovalent" means the antigenic proteins are derived from a single Norovirus genogroup. For example, the VLPs contain VP1 and/or VP2 from a virus strain of genogroup I (e.g., VP1 and VP2 from Norwalk virus). Preferably the VLP is comprised of predominantly VP1 proteins. In one embodiment of the invention, the antigen is a mixture of monovalent VLPs wherein the composition includes VLPs comprised of VP1 and VP2 from a single Norovirus genogroup mixed with VLPs comprised of VP1 and VP2 from a different Norovirus genogroup (e.g. Norwalk virus and Houston virus) taken from multiple viral strains. Purely by way of example the composition can contain monovalent VLPs from one or more strains of Norovirus genogroup I together with monovalent VLPs from one or more strains of Norovirus genogroup II. Preferably, the Norovirus VLP mixture is composed of the strains of Norwalk and Houston Noroviruses.

However, in an alternative embodiment of the invention, the VLPs may be multivalent VLPs that comprise, for example, VP1 and/or VP2 proteins from one Norovirus genogroup intermixed with VP1 and/or VP2 proteins from a second Norovirus genogroup, wherein the different VP I and VP2 proteins are not chimeric VP1 and VP2 proteins, but associate together within the same capsid structure to form immunogenic VLPs. As used herein, the teen "multivalent" means that the antigenic proteins are derived from two or more Norovirus genogroups or strains. Multivalent VLPs may contain VLP antigens taken from two or more viral strains Purely by way of example the composition can contain multivalent VLPs comprised of capsid monomers or multimers from one or more strains of Norovirus genogroup I (e.g. Norwalk virus) together with capsid monomers or multimers from one or more strains of Norovirus genogroup II (e.g. Houston virus). Preferably, the multivalent VLPs contain capsid proteins from the strains of Norwalk and Houston Noroviruses.

The combination of monovalent or multivalent VLPs within the composition preferably would not reduce the immunogenicity of each VLP type. In particular it is preferred that there is no interference between Norovirus VLPs in the combination of the invention, such that the combined VLP composition of the invention is able to elicit immunity against infection by each Norovirus genotype represented in the vaccine. Suitably the immune response against a given VLP type in the combination is at least 50% of the immune response of that same VLP type when measured individually, preferably 100% or substantially 100%. The immune response may suitably be measured, for example, by antibody responses, as illustrated in the examples herein.

Multivalent VLPs may be produced by separate expression of the individual capsid proteins followed by combination to form VLPs. Alternatively multiple capsid proteins may be expressed within the same cell, from one or more DNA constructs. For example, multiple DNA constructs may be transformed or transfected into host cells, each vector encoding a different capsid protein. Alternatively a single vector having multiple capsid genes, controlled by a shared promoter or multiple individual promoters, may be used. IRES elements may also be incorporated into the vector, where appropriate. Using such expression strategies, the co-expressed capsid proteins may be co-purified for subsequent VLP formation, or may spontaneously form multivalent VLPs which can then be purified.

A preferred process for multivalent VLP production comprises preparation of VLP capsid proteins or derivatives, such as VP 1 proteins, from different Norovirus genotypes, mixing the proteins, and assembly of the proteins to produce multivalent VLPs. The VP1 proteins may be in the form of a crude extract, be partially purified or purified prior to mixing. Assembled monovalent VLPs of different genogroups may be disassembled, mixed together and reassembled into multivalent VLPs. Preferably the proteins or VLPs are at least partially purified before being combined. Optionally, further purification of the multivalent VLPs may be carried out after assembly.

Suitably the VLPs of the invention are made by disassembly and reassembly of VLPs, to provide homogenous and pure VLPs. In one embodiment multivalent VLPs may be made by disassembly of two or more VLPs, followed by combination of the disassembled VLP components at any suitable point prior to reassembly. This approach is suitable when VLPs spontaneously form from expressed VP1 protein, as occurs for example, in some yeast strains. Where the expression of the VP 1 protein does not lead to spontaneous VLP formation, preparations of VP1 proteins or capsomers may be combined before assembly into VLPs.

Where mutivalent VLPs are used, preferably the components of the VLPs are mixed in the proportions in which they are desired in the final mixed VLP. For example, a mixture of the same amount of a partially purified VP1 protein from Norwalk and Houston viruses (or other Norovirus strains) provides a multivalent VLP with approximately equal amounts of each protein.

Compositions comprising multivalent VLPs may be stabilized by solutions known in the art, such as those of WO 98/44944, WO 00/45841, incorporated herein by reference.

Compositions of the invention may comprise other proteins or protein fragments in addition to VP1 and VP2 proteins or derivatives. Other proteins or peptides may also be co-administered with the composition of the invention. Optionally the composition may also be formulated or co-administered with non-Norovirus antigens. Suitably these antigens can provide protection against other diseases.

The VP1 protein or functional protein derivative is suitably able to form a VLP, and VLP formation can be assessed by standard techniques such as, for example, electron microscopy and dynamic laser light scattering.

Antigen Preparation

The antigenic molecules of the present invention can be prepared by isolation and purification from the organisms in which they occur naturally, or they may be prepared by recombinant techniques. Preferably the Norovirus VLP antigens are prepared from insect cells such as Sf9 or H5 cells, although any suitable cells such as *E. coli* or yeast cells, for example, *S. cerevisiae, S. pombe, Pichia pastori* or other *Pichia* expression systems, mammalian cell expression such as CHO or HEK systems may also be used. When prepared by a recombinant method or by synthesis, one or more insertions, deletions, inversions or substitutions of the amino acids constituting the peptide may be made. Each of the aforementioned antigens is preferably used in the substantially pure state.

The procedures of production of norovirus VLPs in insect cell culture have been previously disclosed in U.S. Pat. No. 6,942,865, which is incorporated herein by reference in its entirety. Briefly, a cDNA from the 3' end of the genome containing the viral capsid gene (ORF2) and a minor structural gene (ORF3) were cloned. The recombinant baculoviruses carrying the viral capsid genes were constructed from the cloned cDNAs. Norovirus VLPs were produced in Sf9 or H5 insect cell cultures.

Adjuvants

The invention further provides a composition comprising adjuvants for use with the Norovirus antigen. Most adjuvants contain a substance designed to protect the antigen from rapid catabolism, such as aluminum hydroxide or mineral oil, and a stimulator of immune responses, such as Bordatella pertussis or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, and liposomes. Preferably, the adjuvants are bacterially-derived exotoxins. Also preferred are adjuvants which stimulate a Th 1 type response such as 3DMPL or QS21.

Monophosphoryl Lipid A (MPL), a non-toxic derivative of lipid A from *Salmonella*, is a potent TLR-4 agonist that has been developed as a vaccine adjuvant (Evans et al. 2003). In preclinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MPL in intranasal formulations should provide rapid induction of innate responses, eliciting nonspecific immune responses from viral challenge while enhancing the specific responses generated by the antigenic components of the vaccine.

Accordingly, in one embodiment, the present invention provides a composition comprising monophosphoryl lipid A (MPL®) or 3 De-O-acylated monophosphoryl lipid A (3D-MPL®) as an enhancer of adaptive and innate immunity. Chemically 3D-MPL® is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a composition comprising synthetic lipid A, lipid A mimetics or analogs, such as BioMira's PET Lipid A, or synthetic derivatives designed to function like TLR-4 agonists.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation). Suitably effective increases in immunoglobulin levels include by more than 5%, preferably by more than 25%, and in particular by more than 50%, as compared to the same antigen composition without any adjuvant.

Delivery Agent

The invention also provides a composition comprising a delivery agent which functions to enhance antigen uptake, provide a depot effect, or increase antigen retention time at the site of delivery (e.g., delay expulsion of the antigen). Such a delivery agent may be a bioadhesive agent. In particular, the bioadhesive may be a mucoadhesive agent such as chitosan, a chitosan salt, or chitosan base (e.g. chitosan glutamate).

Chitosan, a positively charged linear polysaccharide derived from chitin in the shells of crustaceans, is a bioadhesive for epithelial cells and their overlaying mucus layer. Formulation of antigens with chitosan increases their contact time with the nasal membrane, thus increasing uptake by virtue of a depot effect (Ilium et al. 2001; 2003; Davis et al. 1999; Bacon et al. 2000; van der Lubben et al. 2001; 2001; Lim et al. 2001). Chitosan has been tested as a nasal delivery system for several vaccines, including influenza, pertussis and diphtheria, in both animal models and humans (Ilium et al. 2001; 2003; Bacon et al. 2000; Jabbal-Gill et al. 1998; Mills et al. 2003; McNeela et al. 2004). In these trials, chitosan was shown to enhance systemic immune responses to levels equivalent to parenteral vaccination. In addition, significant antigen-specific IgA levels were also measured in mucosal secretions. Thus, chitosan can greatly enhance a nasal vaccine's effectiveness. Moreover, due to its physical characteristics, chitosan is particularly well suited to intranasal vaccines formulated as powders (van der Lubben et al. 2001; Mikszta et al. 2005; Huang et al. 2004).

Accordingly, in one embodiment, the present invention provides an antigenic or vaccine composition adapted for intranasal administration, wherein the composition includes antigen and an effective amount of adjuvant. In preferred embodiments, the invention provides an antigenic or vaccine composition comprising Norovirus antigen such as Norovirus VLP, in combination with at least one delivery agent, such as chitosan, and at least one adjuvant, such as MPL®, CPGs, imiquimod, gardiquimod, or synthetic lipid A or lipid A mimetics or analogs.

The molecular weight of the chitosan may be between 10 kDa and 800 kDa, preferably between 100 kDa and 700 kDa and more preferably between 200 kDa and 600 kDa. The concentration of chitosan in the composition will typically be up to about 80% (w/w), for example, 5%, 10%, 30%, 50%, 70% or 80%. The chitosan is one which is preferably at least 75% deacetylated, for example 80-90%, more preferably 82-88% deacetylated, particular examples being 83%, 84%, 85%, 86% and 87% deacetylation.

Vaccine and Antigenic Formulations

The compositions of the invention can be formulated for administration as vaccines or antigenic formulations. As used herein, the term "vaccine" refers to a formulation which contains Norovirus VLPs or other Norovirus antigens of the present invention as described above, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or antigen. As used herein, the term "antigenic formulation" or "antigenic composition" refers to a preparation which, when administered to a vertebrate, e.g. a mammal, will induce an immune response. As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-lymphocytes and/or other cells, such as macrophages, against an infectious agent, exhibited by a vertebrate (e.g., a human), that prevents or ameliorates infection or reduces at least one symptom thereof. In particular, "protective immunity" or "protective immune response" refers to immunity or eliciting an immune response against an infectious agent, which is exhibited by a vertebrate (e.g., a human), that prevents or ameliorates an infection or reduces at least one symptom thereof. Specifically, induction of a protective immune response from administration of the vaccine is evident by elimination or reduction of the presence of one or more symptoms of gastroenteritis or a reduction in the duration or severity of such symptoms. Clinical symptoms of gastroenteritis from Norovirus include nausea, diarrhea, loose stool, vomiting, fever, and general malaise. A protective immune response that reduces or eliminates disease symptoms will reduce or stop the spread of a Norovirus outbreak in a population. Vaccine preparation is generally described in Vaccine Design ("The subunit and adjuvant approach" (eds Powell M. F. & Newman M. J.) (1995) Plenum Press New York). The compositions of the present invention can be formulated, for example, for delivery to one or more of the oral, gastro-intestinal, and respiratory (e.g. nasal) mucosa.

Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

In one embodiment, the Norovirus vaccine or antigenic formulation of the present invention contains one or more Norovirus genogroup antigen(s) as the immunogen, an adjuvant such as MPL®, a biopolymer such as chitosan to promote adhesion to mucosal surfaces, and bulking agents such as mannitol and sucrose. For example, the Norovirus vaccine may be formulated as 10 mg of a dry powder containing one or more Norovirus genogroup antigen(s) (e.g., Norwalk virus, Houston virus, Snow Mountain virus), MPL® adjuvant, chitosan mucoadhesive, and mannitol and sucrose as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 μg MPL® (0.1 to 5% w/w range), and about 100 μg Norovirus antigen (0.05 to 5% w/w range).

Norovirus antigen may be present in a concentration of from about 0.01% (w/w) to about 80% (w/w). In one embodiment, Norovirus antigens can be formulated at dosages of about 5 μg, about 15 μg, about 25 μg, about 50 μg, about 100 μg, about 200 μg, about 500 μg, and about 1 mg per 10 mg dry powder formulation (0.05, 0.15, 0.25, 0.5, 1.0, 2.0, 5.0, and 10.0% w/w) for administration into both nostrils (10 mg per nostril) or about 10 μg, about 30 μg, about 50 μg, about 100 μg, about 200 μg, about 400 μg, about 1 mg, and about 2 mgs (0.1, 0.3, 0.5, 1.0, 2.0, 4.0, 10.0 and 20.0% w/w) per 20 mg dry powder formulation for administration into one nostril. The formulation may be given in one or both nostrils during each administration. There may be a booster administration 1 to 12 weeks after the first administration to improve the immune response. The content of each Norovirus antigen in the vaccine and antigenic formulations may be in the range of 1 μg to 100 mg, preferably in the range 1-1000 μg, more preferably 5-500 μg, most typically in the range 10-200 μg. Total Norovirus antigen administered at each dose can be either about 10 μg, about 30 μg, about 200 μg, about 250 μg, about 400 μg, about 500 μg, or about 1000 μg. The total vaccine dose can be administered into one nostril or can be split in half for administration to both nostrils. Dry powder characteristics are such that less than 10% of the particles are less than 10 μm in diameter. Mean particle sizes range from 10 to 500 μm in diameter.

In another embodiment, the antigenic and vaccine compositions can be formulated as a liquid for subsequent administration to a subject. A liquid formulation intended for intranasal administration would comprise Norovirus genogroup antigen(s), adjuvant, and a delivery agent such as chitosan. Liquid formulations for intramuscular (i.m.) administration would comprise Norovirus genogroup antigen(s), adjuvant, and a buffer, without a delivery agent (e.g., chitosan).

Preferably the antigenic and vaccine compositions hereinbefore described are lyophilized and stored anhydrous until they are ready to be used, at which point they are reconstituted with diluent. Alternatively, different components of the composition may be stored separately in a kit (any or all components being lyophilized). The components may remain in lyophilized form for dry formulation or be reconstituted for liquid formulations, and either mixed prior to use or administered separately to the patient. For dry powder administration, the vaccine or antigenic formulation may be preloaded into an intranasal delivery device and stored until use. Preferably, such intranasal delivery device would protect and ensure the stability of its contents.

The lyophilization of antigenic formulations and vaccines is well known in the art. Typically the liquid antigen is freeze dried in the presence of agents to protect the antigen during the lyophilization process and to yield a cake with desirable powder characteristics. Sugars such as sucrose, mannitol, trehalose, or lactose (present at an initial concentration of 10-200 mg/mL) are commonly used for cryoprotection of protein antigens and to yield lyophilized cake with desirable powder characteristics. Lyophilizing the compositions theoretically results in a more stable composition. While the goal of most formulation processes is to minimize protein aggregation and degradation, the inventors have discovered that the presence of aggregated antigen enhances the immune response to Norovirus VLPs (see Examples 3 and 4). Therefore, the inventors have developed methods by which the percentage of aggregation of the antigen can be controlled during the lyophilization process to produce an optimal ratio of aggregated antigen to intact antigen to induce a maximal immune response.

Thus, the invention also encompasses a method of making Norovirus antigen formulations comprising (a) preparing a pre-lyophilization solution comprising Norovirus antigen, sucrose, and chitosan, wherein the ratios of sucrose to chitosan are from about 0:1 to about 10:1; (b) freezing the solution with liquid nitrogen; and (c) lyophilizing the frozen solution at ambient temperature for 48-72 hours, wherein the final lyophilized product contains a percentage of said Norovirus antigen in aggregated form. In one embodiment, the pre-lyophilization solution further comprises a bulking agent. In another embodiment, said bulking agent is mannitol.

Appropriate ratios of sucrose and chitosan to yield desired percentages of aggregation can be determined by the following guidelines. A pre-lyophilization mixture containing a weight ratio of sucrose to chitosan in a range from about 2.5:1 to about 10:1 will yield greater than 95% intact Norovirus antigen post-lyophilization (i.e. less than 5% aggregated antigen; see Example 13). A range of sucrose to chitosan weight ratios of about 1:1 to about 2.1:1 will yield about 50% to about 90% intact Norovirus antigen (i.e. about 10% to about 50% aggregated antigen). Weight ratios of 0:1 sucrose to chitosan will produce less than 30% of intact Norovirus antigen. Omission of both sucrose and chitosan will produce less than 5% intact antigen (i.e. greater than 95% aggregated antigen). Using these guidelines, the skilled artisan could adjust the sucrose to chitosan weight ratios in the pre-lyophilization mixture to obtain the desired amount of aggregation necessary to produce an optimal immune response.

In addition, the inclusion of sucrose and chitosan to the pre-lyophilization solution promotes the stability of the intact Norovirus antigen over time. The ratio of aggregated antigen/intact antigen in the formulation does not increase when stored as a dry powder for a period of about 12 months or greater (see Example 10). Thus, this lyophilization procedure ensures stable formulations with predictable and controllable ratios of aggregated to intact Norovirus antigen.

Methods of Stimulating an Immune Response

The amount of antigen in each antigenic or vaccine formulation dose is selected as an amount which induces a robust immune response without significant, adverse side effects. Such amount will vary depending upon which specific antigen(s) is employed, route of administration, and adjuvants used. In general, the dose administered to a patient, in the context of the present invention should be sufficient to effect a protective immune response in the patient over time, or to induce the production of antigen-specific antibodies. Thus, the composition is administered to a patient in an amount sufficient to elicit an immune response to the specific antigens and/or to prevent, alleviate, reduce, or cure symptoms and/or complications from the disease or infection, and thus reduce or stop the spread of a Norovirus outbreak in a population. An amount adequate to accomplish this is defined as a "therapeutically effective dose."

For a substantially pure form of the Norovirus antigen, it is expected that each dose will comprise about 1 µg to 10 mg, preferably about 15-500 µg for each Norovirus antigen in the formulation. In a typical immunization regime employing the antigenic preparations of the present invention, the formulations may be administered in several doses (e.g. 1-4), each dose containing 1-1000 µg of each antigen. The dose will be determined by the immunological activity the composition produced and the condition of the patient, as well as the body weight or surface areas of the patient to be treated. The size of the dose also will be determined by the existence, nature, and extent of any adverse side effects that may accompany the administration of a particular composition in a particular patient.

The antigenic and vaccine formulations of the present invention may be administered via a non-mucosal or mucosal route. These administrations may include in vivo administration via parenteral injection (e.g. intravenous, subcutaneous, and intramuscular) or other traditional direct routes, such as buccal/sublingual, rectal, oral, nasal, topical (such as transdermal and ophthalmic), vaginal, pulmonary, intraarterial, intraperitoneal, intraocular, or intranasal routes or directly into a specific tissue. Alternatively, the vaccines of the invention may be administered by any of a variety of routes such as oral, topical, subcutaneous, mucosal, intravenous, intramuscular, intranasal, sublingual, transcutaneous, subdermal, intradermal and via suppository. Administration may be accomplished simply by direct administration using a needle, catheter or related device, at a single time point or at multiple time points.

In a preferred embodiment, the antigenic and vaccine formulations of the present invention are administered by the intranasal route. Immunization via the mucosal surfaces offers numerous potential advantages over other routes of immunization. The most obvious benefits are 1) mucosal immunization does not require needles or highly-trained personnel for administration, and 2) immune responses are raised at the site(s) of pathogen entry, as well as systemically (Isaka et al. 1999; Kozlowski et al. 1997; Mestecky et al. 1997; Wu et al. 1997).

In a further aspect, the invention provides a method of eliciting an IgA mucosal immune response and an IgG systemic immune response by administering (preferably intranasally) to a mucosal surface of the patient an antigenic or vaccine composition comprising one or more Norovirus antigens, at least one effective adjuvant and/or at least one delivery agent.

The present invention also contemplates the provision of means for dispensing intranasal formulations of Norovirus antigens hereinbefore defined, and at least one adjuvant or at least one delivery agent as hereinbefore defined. A dispensing device may, for example, take the form of an aerosol delivery system, and may be arranged to dispense only a single dose, or a multiplicity of doses. Such a device would deliver a metered dose of the vaccine or antigenic formulation to the nasal passage. Other examples of appropriate devices include, but are not limited to, droppers, swabs, aerosolizers, insufflators (e.g. Valois Monopowder Nasal Administration Device, single dose Bespak UniDose DP dry powder intranasal delivery device), nebulizers, and inhalers. The devices may deliver the antigenic or vaccine formulation by passive means requiring the subject to inhale the formulation into the nasal cavity. Alternatively, the device may actively deliver the formulation by pumping or spraying a dose into the nasal cavity. The antigenic formulation or vaccine may be delivered into one or both nostrils by one or more such devices. Administration could include two devices per subject (one device per nostril). Actual dose of active ingredient (Norovirus antigen) may be about 5-1000 µg. In a preferred embodiment, the antigenic or vaccine formulation is administered to the nasal mucosa by rapid deposition within the nasal passage from a device containing the formulation held close to the nasal passageway.

The invention also provides a method of generating antibodies to one or more Norovirus antigens, said method comprising administration of a vaccine or antigenic formulation of the invention as described above to a subject. These antibodies can be isolated and purified by routine methods in the art. The isolated antibodies specific for Norovirus antigens can be used in the development of diagnostic immunological assays. These assays could be employed to detect a Norovirus in clinical samples and identify the particular virus causing the infection (e.g. Norwalk, Houston, Snow Mountain, etc.). Alternatively, the isolated antibodies can be administered to subjects susceptible to Norovirus infection to confer passive or short-term immunity.

The invention provides methods for eliciting protective immunity to a Norovirus infection in a subject comprising administering a vaccine to the subject, wherein said vaccine comprises Norovirus VLPs and at least one adjuvant. In one embodiment, the subject is a human and the vaccine confers protection from one or more symptoms of Norovirus infection. Although others have reported methods of inducing an immune response with Norovirus antigens (see U.S. Patent Application Publication No. US 2007/0207526), no one has demonstrated the induction of a protective immune response in humans. Unlike several vaccines currently licensed in the U.S. where effectiveness of the vaccine correlates with serum antibodies, studies have shown that markers of an immune response, such as increased titers of serum antibodies against Norwalk virus, are not associated with protective immunity in humans (Johnson et al. (1990) J. Infectious Diseases 161: 18-21). Moreover, another study examining Norwalk viral challenge in humans indicated that susceptibility to Norwalk infection was multifactorial and included factors such as secretor status and memory mucosal immune response (Lindesmith et al. (2003) Nature Medicine 9: 548-553). Because Norovirus is not able to be cultured in vitro, no viral neutralization assays are currently available. A functional assay which serves as a substitute for the neutralization assay is the hemagglutination inhibition (HAI) assay. HAI measures the ability of Norovirus vaccine-induced antibodies to inhibit the agglutination of antigen-coated red blood cells by Norovirus VLPs because Norovirus VLPs bind to red blood cell antigens. In this assay, a fixed amount of Norovirus VLPs is mixed with a fixed amount of red blood cells and serum from immunized subjects. If the serum sample contains functional antibodies, the antibodies will compete with the VLPs for binding to the red blood cells, thereby inhibiting the agglutination of the red blood cells.

Similar findings have been observed with vaccines for other viruses, such as rotavirus. For rotavirus vaccines, there is controversy over whether serum antibodies are directly involved in protection or merely reflect recent infection (Jiang, 2002; Franco, 2006). Defining such correlates of protection is particularly difficult in the context of diarrheal diseases such as rotavirus or norovirus, where preclinical studies inferring protection may be multifaceted with contributions from mucosal immunity (such as intestinal IgA), cytokine elaboration, and cell mediated immunity. The difficulty in measuring such immune responses during clinical development, and the lack of correlation to serum antibody measurements, requires that the effectiveness of a vaccine for these types of viruses can only be demonstrated through human clinical challenge experiments.

As mentioned above, administration of the vaccine of the present invention prevents and/or reduces at least one symptom of Norovirus infection. Symptoms of Norovirus infection are well known in the art and include nausea, vomiting, diarrhea, and stomach cramping. Additionally, a patient with a Norovirus infection may have a low-grade fever, headache, chills, muscle aches, and fatigue. The invention also encompasses a method of inducing a protective immune response in a subject experiencing a Norovirus infection by administering to the subject a vaccine formulation of the invention such that at least one symptom associated with the Norovirus infection is alleviated and/or reduced. A reduction in a symptom may be determined subjectively or objectively, e.g., self-assessment by a subject, by a clinician's assessment or by conducting an appropriate assay or measurement (e.g. body temperature), including, e.g., a quality of life assessment, a slowed progression of a Norovirus infection or additional symptoms, a reduced severity of Norovirus symptoms or suitable assays (e.g. antibody titer, RT-PCR antigen detection, and/or B-cell or T-cell activation assay). An effective response may also be determined by directly measuring (e.g., RT-PCR) virus load in stool samples, which reflects the amount of virus shed from the intestines). The objective assessment comprises both animal and human assessments.

Stability and efficacy in animal models of the vaccine and antigenic formulations disclosed herein are reported in International Application No. PCT/US07/79929, which is herein incorporated by reference in its entirety.

EXAMPLES

The invention will now be illustrated in greater detail by reference to the specific embodiments described in the following examples. The examples are intended to be purely illustrative of the invention and are not intended to limit its scope in any way.

Example 1. GLP Toxicity Study of Norovirus Vaccine Formulations in Rabbits

The purpose of this study was to evaluate the potential toxicity of a Norwalk virus-virus-like particle (NV-VLP) vaccine following three intranasal doses in rabbits. The NV-VLP vaccine contained (per 10 mg dry powder) 25 µg of a Genogroup I VLP, 25 µg MPL, 7 mg chitosan glutamate, 1.475 mg mannitol, and 1.475 mg sucrose. The study was conducted over an eight week period. The persistence, reversibility, or delayed onset of any effects were assessed after a four-week, no-treatment recovery interval. Sixty New Zealand White rabbits (30/sex) were randomly assigned to three groups (10 rabbits/sex/group). Group 1 animals were not dosed (i.e. naive). Group 2 animals were administered 10 mg/nostril (20 mg total) of placebo (i.e. adjuvant/excipient: MPL, chitosan, sucrose, and mannitol). Group 3 animals were administered 10 mg/nostril (20 mg total) of NV-VLP vaccine, which represented 25 pig of antigen per nostril (50 µg total). Animals in groups 2 and 3 were dosed on study day (SD) 1, 22, and 43 by intranasal administration using the Bespak Unidose intranasal dry powder device. Animals (5/group/sex) were subjected to a full gross necropsy on SD 46 and 74. Parameters evaluated during the study included mortality, clinical and cageside observations, body weights, body weight changes, food consumption, body temperature, ophthalmology examinations, clinical pathology (clinical chemistry, hematology, and urinalysis), gross pathology, organ weight data, and histopathology. The study outline is summarized in Table 1. The conclusions of the study are summarized in Table 2.

TABLE 1

Study Parameters for GLP Toxicity
Study of Norwalk Vaccine Formulation

| | |
|---|---|
| Species | SPF New Zealand White Rabbits with ear tag IDs |
| No. Animals/Sex/Dose Group | 10 males and 10 females/group |
| Total Number of Animals in Study | 60 |
| Group 1 | Non-treated controls |
| Group 2 | Adjuvant/Excipient |
| Group 3 | 1x maximum human dose VLPs in Adjuvant/Excipient |

TABLE 2

Safety and Toxicology Findings for Norwalk Vaccine Formulation

| | |
|---|---|
| Observations | No treatment related effects on mortality, clinical or cageside observations. |
| Body weight and body weight changes | No adverse effect on body weights or body weight changes. |
| Food consumption | No treatment related adverse effect on food consumption. |
| Body temperature | No treatment related adverse effect on body temperature. |
| Opthamology | No ocular lesions were noted in any animal over the course of the study. |
| Clinical Pathology | Polyclonal activation of B lymphocyte populations in rabbits receiving NV-VLP Vaccine or Adjuvant/Excipient was noted days 3-76. Absolute monocyte values were elevated in rabbits receiving NV-VLP Vaccine or Adjuvant/Excipient on days 3-46. There were no treatment effects on selected urinalysis parameters. |
| Gross Pathology | No treatment related observations. |
| Organ weights | No adverse effects on absolute or relative organ weights. |
| Histopathology | Varying degrees of inflammatory infiltrates, either within the lamina propria of nasal turbinates or free within the nasal passages, and/or hemorrhage within the nasal passages of rabbits receiving NV-VLP Vaccine or Adjuvant/Excipient. The observed lesions are those that would be expected in an immunologic reaction. Lesions in both groups were limited in nature and resolved completely by SD 74. |

Cage side observations revealed no significant findings. Hematological measures (increases in globulin and total protein) were typical of B lymphocyte polyclonal activation and may be attributable to adjuvant effects. Histopathology findings consisted of varying degrees of inflammatory infiltrates, either within the lamina propria of nasal turbinates or free within the nasal passages, and/or mild hemorrhage in the nasal passages of rabbits in both groups. The observed lesions would be expected in an immunologic reaction. Lesions in both groups were limited in nature and resolved completely by study day 74.

Serological samples analyzed by ELISA for NV-VLP specific IgG showed measurable anti-NV-VLP titers in 30% of the immunized animals on day 10 following a single dose (see FIG. 1). Boost treatments on days 22 and 43 increased both the number of seroconverted animals and levels of product-specific antibodies, and by day 73, 90% of the immunized animals seroconverted. None of the naïve or matrix treated controls had quantifiable levels of NV-VLP specific antibodies (data not shown).

The immune response was further characterized by evaluating memory B-cell responses in an additional set of rabbits immunized intranasally with the same formulation on days 1, 15 and 29. Memory B-cell responses were measured as described in International Application No. PCT/US07/79929, which is herein incorporated by reference in its entirety. Tissues collected 156 days after the last boost showed the presence of NV-VLP-specific memory B-cells in the peripheral blood, the spleen, and most notably, in the mesenteric lymph nodes. The antigen-specific memory B-cells in the mesenteric lymph nodes were IgA positive. Additionally, NV-VLP-specific antibody-secreting long-lived plasma cells were present in the bone marrow.

Example 2. Dose Escalation Safety Study of Norwalk Vaccine Formulation in Humans A double-blind, controlled, dose-escalation phase 1 study of the safety and immunogenicity of a Norovirus genogroup 1 vaccine was conducted. The vaccine consisted of lyophilized Norwalk virus-like particles (VLPs) in a dry powder matrix designed for intranasal administration. Vaccinees included healthy adult volunteers who were H type 1 antigen secretors. The rationale for enrollment of H type 1 antigen secretors is that H type 1 antigen secretors are susceptible to Norwalk viral infections while non-secretors are resistant. As a control, 2 additional volunteers at each dosage level received matrix alone. The dry powder matrix included 25 μg MPL® adjuvant, 7 mg chitosan, 1.5 mg mannitol, and 1.5 mg sucrose. Volunteers were dosed on days 0 and 21 and were required to keep a 7-day diary of symptoms after each dose. Blood for serology, antibody secreting cells (ASC), and stool and saliva samples for mucosal antibody evaluation were collected.

The components of the Norwalk VLP vaccine are listed in Table 3. The vaccine is packaged in an intranasal delivery device. Single administrations of Norwalk VLP Vaccine were packaged in a single dose Bespak (Milton Keynes, UK) UniDose DP dry powder intranasal delivery device. Each device delivered 10 mg of the dry powder vaccine formulation. Each dose of vaccine consisted of two delivery devices, one in each nostril. The total vaccine dose was 20 mg of dry power. The formulation of Adjuvant/Excipient is the same as the Norwalk VLP Vaccine except that no Norwalk VLP antigen is included in the formulation. The formulation of the Adjuvant/Excipient (also referred to as dry powder matrix) is summarized in Table 4.

TABLE 3

Norwalk VLP Vaccine Composition

| Component | Molecular class | Quantity per 10 mg dry powder | % of Final Formulation |
|---|---|---|---|
| Norwalk VLP | Recombinant protein | 2.5, 7.5, 25, or 50 μg | 0.025, 0.075, 0.25, or 0.50% |
| Monophosphoryl Lipid A | Phospholipid | 25 μg | 0.25% |
| Chitosan | Polysaccharide | 7.0 mg | 70% |
| Mannitol | Sugar | 1.5 mg | 15%* |
| Sucrose | Sugar | 1.5 mg | 15% |

TABLE 4

Adjuvant/Excipient (dry powder matrix)

| Component | Molecular class | Quantity per 10 mg dry powder | % of Final Formulation |
|---|---|---|---|
| Monophosphoryl Lipid A | Phospholipid | 25 μg | 0.25% |
| Chitosan | Polysaccharide | 7.0 mg | 70% |
| Mannitol | Sugar | 1.5 mg | 15% |
| Sucrose | Sugar | 1.5 mg | 15% |

Specifically, the dose escalation of the vaccine was conducted as follows: After appropriate screening for good health, a group of 3 volunteers was randomized to receive either 5 μg Norwalk VLP Vaccine plus dry powder matrix (n=2) or dry powder matrix alone (n=1) by the intranasal route. These 3 volunteers were followed for safety for 21 days and their safety data reviewed by the Independent Safety Monitor (ISM). Upon approval of the ISM, these individuals received their second dose of Vaccine or matrix on day 21, and 4 additional volunteers were randomized to receive either 5 μg VLP protein plus dry powder matrix (n=3) or matrix alone (n=1) by the intranasal route. The ISM reviewed the safety data from this second group and upon approval of the ISM, the second intranasal dose was given 21 days after the first dose. Volunteers kept a 7-day diary of symptoms after each dose. After the ISM determined that escalation to the next higher dose was acceptable, another group of 7 volunteers was randomized to receive either Norwalk VLP Vaccine containing 15 μg VLP protein (n=5) or dry powder matrix alone (n=2) by the intranasal route at day 0 and day 21. Again, 7-day symptom diaries were recorded and reviewed by the ISM before the second dose at day 21. Finally, after review of the safety data from the first two dosage cohorts, the ISM determined that dose escalation was acceptable and a final group of 7 volunteers were randomized to receive either Norwalk VLP Vaccine containing 50 μg VLP protein (n=5) or dry powder matrix alone (n=2) by the intranasal route on day 0 and day 21. Seven-day symptom diaries and other safety data were again reviewed by the ISM before the second dose at day 21.

The volunteers kept a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving Norwalk VLP Vaccine or dry powder matrix alone. Interim medical histories were obtained at each follow-up visit (days 7±1, 21±2, 28±2, 56±2 and 180±14); volunteers were queried about interim illness, medications, and doctor's visits. Volunteers were asked to report all serious or severe adverse events including events that were not solicited during follow up visits. Volunteers had CBC and serum creatinine, glucose, AST, and ALT assessed on days 7 and 28 (7 days after each immunization) and, if abnormal, the abnormal laboratory test was followed until the test became normal or stabilized.

The blinded data indicated that of the volunteers that received the low dose (n=5) or matrix (n=2), 4 of 7 reported some or all of the following: nasal discharge, nasal pain, stuffiness, itching, sneezing, headache, and/or sore throat in the first 24 hours after vaccination. One volunteer reported a minor nosebleed on each of days 1 and 6. Of the volunteers that received the middle dose (n=5) or matrix (n=2), 5 of 7 reported mild nasal discharge, stuffiness, itching, sneezing, and/or headache in the first 24 hours. Symptoms generally resolved in the first 72 hours, but stuffiness persisted to day 7 in one volunteer. A summary of the findings on the unblinded data is presented in Table 5 below, which also includes adverse events reported in the high dose. These findings indicate that intranasal Norovirus VLP vaccine is associated with local, usually mild, short-lived symptoms that appeared to be independent of VLP concentration. No differences were seen between the adjuvant/excipient (or matrix) control group and the Norwalk VLP vaccine groups for adverse events, hematology, blood chemistry and/or physical examination results.

TABLE 5

Number of Volunteers with Adverse Events to Norwalk VLP Vaccine or Adjuvant/Excipient

| Reported Adverse Events | Adjuvant/ Excipient (N = 6) | Low Dose (N = 5) | Mid Dose (N = 5) | High Dose (N = 5)* |
|---|---|---|---|---|
| Nose and Throat | | | | |
| Nasal Stuffiness | 4 | 2 | 3 | 1 |
| Nasal Itching | 3 | 3 | 2 | 2 |
| Nasal Discharge | 3 | 3 | 4 | 3 |
| Nasal Pain | — | 2 | 1 | 2 |
| Sneezing | 3 | 2 | 1 | 3 |
| Nose Bleed | — | 1 | 1 | — |
| Sore Throat/URI | — | 1 | — | 1 |
| Itchy Sore Throat | — | 1 | — | — |
| Burning in Nose/Throat | — | 1 | — | 1 |
| Chest | | | | |
| Cough | 2 | — | — | — |
| Chest discomfort | — | — | — | 1 |
| Systemic | | | | |
| Headache | 2 | 2 | 1 | 1 |
| Malaise | 3 | 2 | — | 1 |
| Nausea | — | 1 | — | 1 |
| Abdominal Cramp | 1 | — | — | 1 |
| Laboratory | | | | |
| ALT/AST | — | 1 | — | — |
| AST | 1 | — | — | — |
| ALT | — | — | — | 1 |
| Alk Phos | — | — | — | 1 |
| Gastrointestinal | | | | |
| Diarrhea | — | 1 | — | 1 |
| Loss of appetite | 1 | — | 1 | — |

TABLE 5-continued

Number of Volunteers with Adverse Events
to Norwalk VLP Vaccine or Adjuvant/Excipient

| Reported Adverse Events | Adjuvant/ Excipient (N = 6) | Low Dose (N = 5) | Mid Dose (N = 5) | High Dose (N = 5)* |
|---|---|---|---|---|
| No Adverse Events Reported | — | — | 1 | 2 |

*One subject in cohort 3 did not receive the second dose

Blood was collected before immunization and on days 7±1, 21±2, 28±2, 56±2, and 180±14 to measure serum antibodies to Norwalk VLP Vaccine by enzyme-linked immunosorbent assays (ELISA). Before and on day 7 after administration of each dose of Vaccine or dry powder matrix alone peripheral blood lymphocytes were collected to detect antibody secreting cells by ELISPOT assay. Before and on days 21±2, 56±2 and 180±14 after vaccination, whole blood was obtained to separate cells and freeze for future studies of cell mediated immunity, including cytokine production in response to Norwalk VLP antigen, and lymphoproliferation. Whole stool samples were collected before immunization and on days 7±1, 21±2, 28±2, 56±2, and day 180±14 for anti-Norwalk VLP sIgA screening. Saliva was collected with a commercially available device (Salivette, Sarstedt, Newton, N.C.) before immunization and on days 7±1, 21±2, 28±2, 56±2, and if positive for mucosal antibodies at day 56, a day 180±14 sample was collected and screened for anti-Norwalk VLP sIgA. Finally blood from volunteers receiving the highest dose of Norwalk VLPs (50 μg, third cohort described above) was screened for memory B-cells on days 0, 21, 56 and 180.

The following methods were used to analyze the blood, stool, and saliva samples collected from immunized individuals or individuals receiving the dry powder matrix alone:

A. Serum Antibody Measurements By ELISA

Figure 2A:
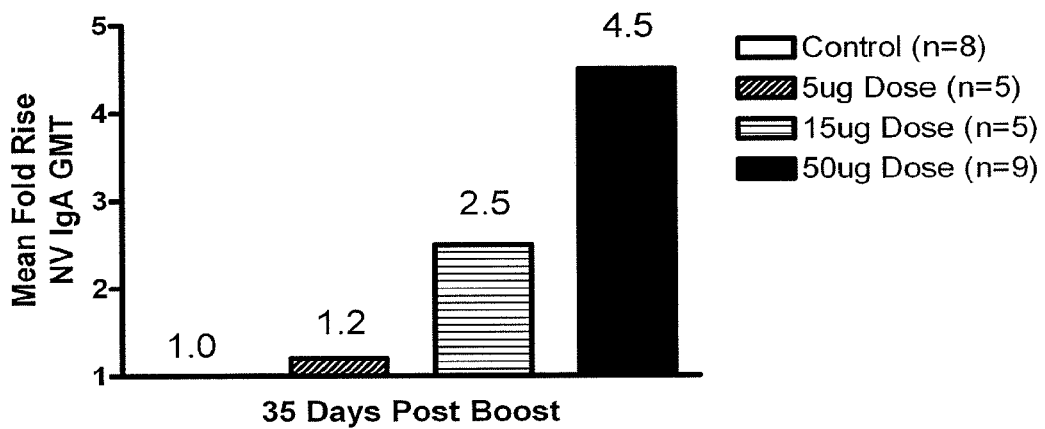
FIGS. 2A-2B depict the results of ELISA assays measuring serum IgA (panel 2A) and IgG (panel 2B) levels from human volunteers immunized with control (adjuvant/excipient) or a vaccine formulation containing one of three doses of Norwalk Virus VLPs (5, 15, or 50 µg). The geometric mean fold-increase in anti-VLP titer is shown for each of the dosage levels at 35 days after the second immunization (day 56). Volunteers received immunizations on days 0 and 21.
Figure 2B:
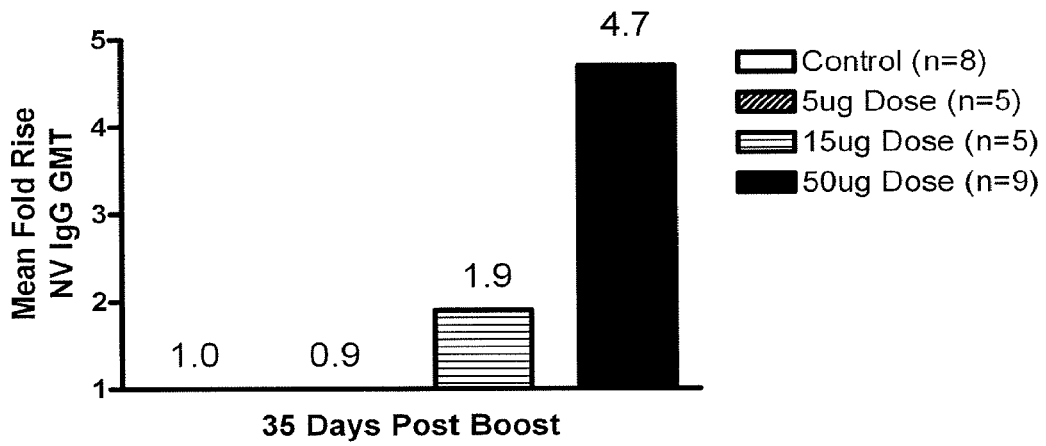

Twenty mL of blood were collected before and at multiple time points after vaccination for measurement of antibodies to Norwalk virus by ELISA, using purified recombinant Norwalk VLPs as target antigen to screen the coded specimens. Briefly, Norwalk VLPs in carbonate coating buffer pH 9.6 were used to coat microtiter plates. Coated plates were washed, blocked, and incubated with serial two-fold dilutions of test serum followed by washing and incubation with enzyme-conjugated secondary antibody reagents specific for human IgG, IgM, and IgA. Appropriate substrate solutions were added, color developed, plates read, and the IgG, IgM, and IgA endpoint titers were determined in comparison to a reference standard curve for each antibody class. A positive response was defined as a 4-fold rise in titer after vaccination. The serum titers at day 56 (35 days after the second immunization) for each of the vaccine doses are shown in FIG. 2. The results show a dose-dependent increase in serum titers for IgG and IgA. A significant serum titer for both IgG and IgA was observed in volunteers receiving the vaccine containing 50 μg of Norovirus antigen.

B. Antibody Secreting Cell Assays

PBMCs were collected from heparinized blood (30 mL for cohorts 1 and 2, 25 mL for cohort 3) for ASC assays to detect cells secreting antibodies to Norwalk VLPs. These assays were performed on days 0, 7±1, 21±2, and 28±2 after administration of Norwalk VLP Vaccine or dry powder matrix alone. The response rate and mean number of ASC per $10^6$ PBMC at each time point for each dosage were described. A positive response was defined as a post-vaccination ASC count per $10^6$ PBMCs that is at least 3 standard deviations (SD) above the mean pre-vaccination count for all subjects (in the log metric) and at least 8 ASC spots, which corresponds to the mean of medium-stimulated negative control wells (2 spots) plus 3 SD as determined in similar assays.

Figure 3A:
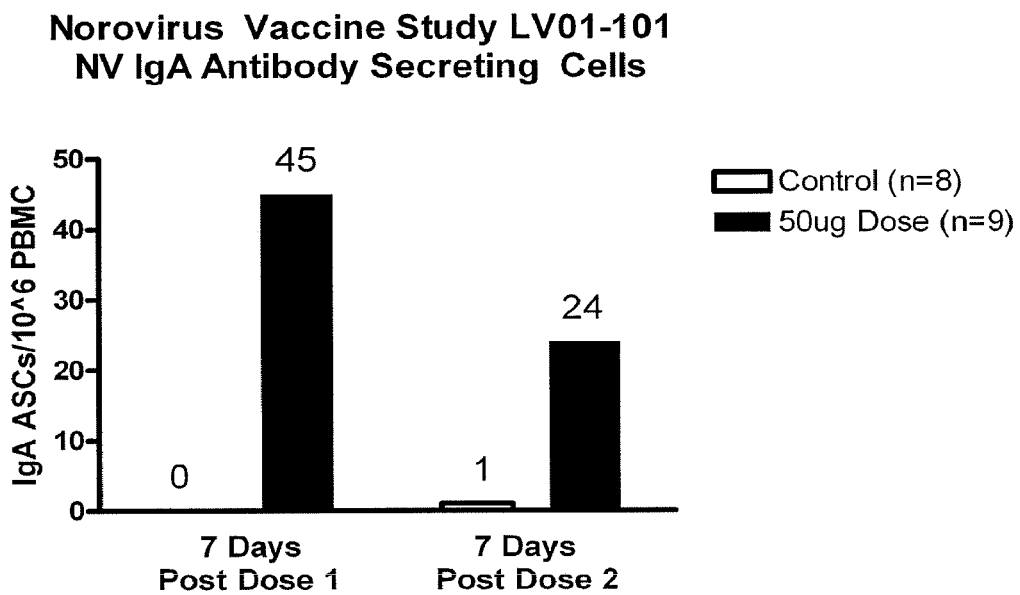
FIGS. 3A-3B show the levels of IgA (panel 3A) and IgG (panel 3B) antibody secreting cells (ASCs) in human volunteers receiving vaccine formulations with the 50 µg dose of Norwalk Virus VLPs or control (adjuvant/excipient). The geometric mean (GMN) of ASCs per $10^6$ peripheral blood mononuclear cells (PBMCs) is plotted versus study day (day 7 or day 28), specifically seven days post immunization. Volunteers received immunizations on days 0 and 21.
Figure 3B:
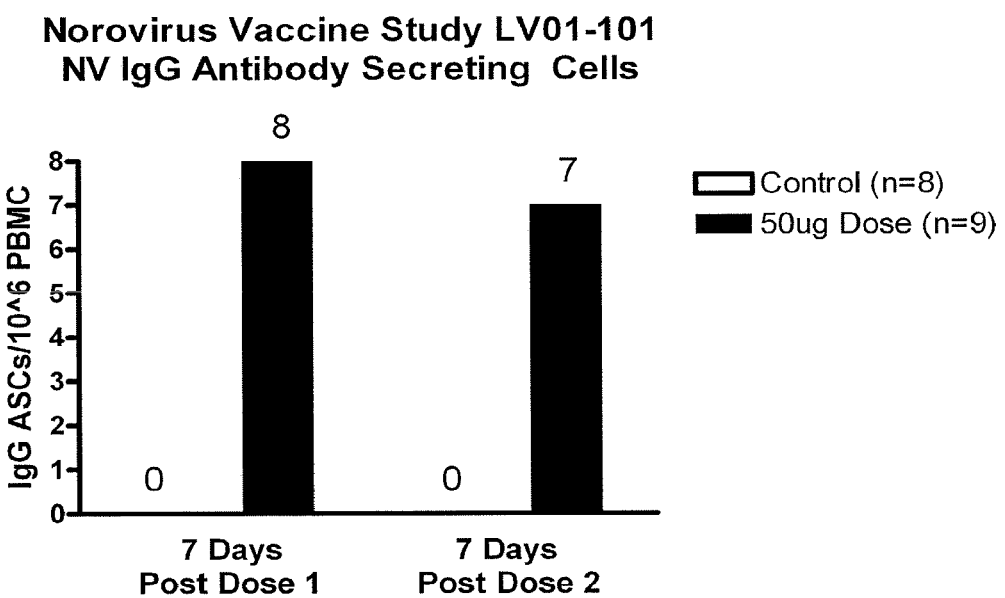

The results of the ASC assays for the 50 μg dose of Norwalk VLPs are depicted in FIG. 3. Circulating IgG and IgA antibody secreting cells were observed seven days after initial and boost vaccinations, suggesting that the vaccine is immunogenic.

C. Measurement of Functional Antibody Response

Serum collected as described in paragraph B, above, was further analyzed to determine the functional properties of the anti-Norwalk virus antibodies. Serial two-fold dilutions of test serum were analyzed with respect to their ability to inhibit hemagglutination of red blood cells by Norwalk VLPs (a functional assay to indicate protective immune responses). A positive response was defined as a 4-fold rise in titer after vaccination. The serum titers and hemagglutination inhibition titers at day 56 (35 days post boost) for five subjects who received the 50 μg dose of the Norwalk VLPs vaccine are shown in Table 6. The results show that seventy five percent (75%) of the individuals who exhibited a seroconversion response as measured by serum IgG titers also developed a functional antibody response capable of blocking the binding receptor on human red blood cells as measured by hemagglutination inhibition.

TABLE 6

Serum IgG and Hemagglutination Inhibition (HAI) (functional) Titers on Day 0 and Day 35 Post Boost (35PB) for Five Human Volunteers.

| Subject Reference | Day 0 | Day 35 PB |
|---|---|---|
| Serum IgG Titers | | |
| A | 2,444.6 | 37,185.9 |
| B | 4,462.1 | 23,508.4 |
| C | 7,735.7 | 13,357.8 |
| D | 884.5 | 4,577.5 |
| E | 12,719.0 | 91,710.8 |
| Hemagglutination Inhibition (HAI) Titers | | |
| A | 8 | 256 |
| B | 8 | 256 |
| C | 512 | 512 |
| D | <8 | 8 |
| E | 128 | 1024 |

D. Measurement of Norwalk Virus-Specific Memory B-Cells

Heparinized blood was collected from cohort 3 (30 mL days 0 and 21, 50 mL days 56 and 180) to measure memory B cells on days 0, 21, 56 and 180 after vaccination using an ELISpot assay preceded by an in vitro antigen stimulation. A similar assay was successfully used to measure frequency of memory B cells elicited by Norwalk VLP formulations in rabbits (See International Application No. PCT/US07/79929, herein incorporated by reference). Peripheral blood mononuclear cells ($5 \times 10^6$ cells/mL, 1 mL/well in 24-well plates) are incubated for 4 days with Norwalk VLP antigen (2-10 μg/mL) to allow for clonal expansion of antigen-specific memory B cells and differentiation into antibody secreting cells. Controls include cells incubated in the same conditions in the absence of antigen and/or cells incubated with an unrelated antigen. Following stimulation, cells are washed, counted and transferred to ELISpot plates coated with Norwalk virus VLP. To determine frequency of virus-specific memory B cells per total Ig-secreting B lymphocytes, expanded B cells are also added to wells coated with anti-human IgG and anti-human IgA antibodies. Bound antibodies are revealed with HRP-labeled anti-human IgG or anti-human IgA followed by True Blue substrate. Conjugates to IgA and IgG subclasses (IgA1, IgA2 and IgG1-4) may also be used to determine antigen-specific subclass responses which may be related with distinct effector mechanisms and locations of immune priming. Spots are counted with an ELISpot reader. The expanded cell populations for each volunteer are examined by flow cytometry to confirm their memory B cell phenotype, i.e. CD19+, CD27+, IgG+, IgM+, CD38+, IgD−.

E. Cellular Immune Responses

Heparinized blood (50 mL cohorts 1 and 2, 25 mL cohort 3) was collected as coded specimens and the peripheral blood mononuclear cells (PBMC) isolated and cryopreserved in liquid nitrogen for possible future evaluation of CMI responses to Norwalk VLP antigen. Assays that may be performed include PBMC proliferative and cytokine responses to Norwalk VLP antigen and can be determined by measuring interferon (IFN)-γ and interleukin (IL)-4 levels according to established techniques.

F. Collections of Stool and Saliva for Anti-Norwalk VLP sIgA

Anti-recombinant Norwalk Virus IgA is measured in stool and saliva samples. Saliva specimens are treated with protease inhibitors (i.e. AEB SF, leupeptin, bestatin, and aprotinin) (Sigma, St. Louis, Mo.), stored at −70° C., and assayed using a modification of a previously described assay (Mills et al. (2003) Infect. Immun. 71: 726-732). Stool is collected on multiple days after vaccination and specimens stored at −70° C. until analysis. The specimens are thawed, and protease inhibitor buffer added to prepare a 10% w/v stool suspension. Stool supernatants are assayed for recombinant Norwalk Virus (rNV)-specific mucosal IgA by ELISA, as described below.

Approximately 2-3 mL of whole saliva was collected before and at multiple time points after vaccination. Saliva was collected by a commercially available device (Salivette, Sarstedt, Newton, N.C.), in which a Salivette swab is chewed or placed under the tongue for 30-45 seconds until saturated with saliva. Saliva was collected from the swab by centrifugation.

G. Measurement of Anti-Norwalk VLP in Stool and Saliva

ELISAs, utilizing plates coated with either anti-human IgA antibody reagents or target rNV VLP antigen coatings, are performed to determine total IgA and to titer the specific anti-VLP IgA responses for each specimen. Total or specific IgA are revealed with HRP-labeled anti-human IgA as described above. An internal total IgA standard curve is included to quantify the IgA content. Response is defined as a 4-fold rise in specific antibody.

Example 3. Safety and Immunogenicity Study of Two Dosages of Intranasal Norwalk VLP 5 Vaccine in Humans A randomized, double blind study in healthy adults is conducted to compare the safety and immunogenicity of two dosage levels of a Norwalk virus-like particle (VLP) vaccine with adjuvant/excipients and placebo controls (empty device). The vaccine consists of Norwalk virus-like particles (VLPs) in a dry powder matrix designed for intranasal administration as described in Example 2. Vaccines include healthy adult volunteers who are H type 1 antigen secretors. The human volunteers are randomly assigned to one of four groups and each group receives one of the following treatments: a 50 µg dose of the Norwalk VLP vaccine, a 100 µg dose of the Norwalk VLP vaccine, the adjuvant/excipient, or placebo. Volunteers are dosed on days 0 and 21 and are required to keep a 7-day diary of symptoms after each dose. Blood for serology, antibody secreting cells (ASC), and stool and saliva samples for mucosal antibody evaluation are collected.

The components of the vaccine are listed in Table 3 in Example 2. The vaccine is packaged in an intranasal delivery device. Single administrations of the Norwalk VLP vaccine are packaged in a single dose Bespak (Milton Keynes, UK) UniDose DP dry powder intranasal delivery device. Each device delivers 10 mg of the dry powder vaccine formulation. Each dose of vaccine consists of two delivery devices, one in each nostril. The total vaccine dose is 20 mg of dry power. Therefore, the 50 µs vaccine dose consists of two devices that each deliver 10 mg of dry powder formulation, wherein each 10 mg of dry powder formulation consists of 25 µg of Norwalk VLP, 25 µg MPL® adjuvant, 7 mg chitosan, 1.5 mg mannitol, and 1.5 mg sucrose. Similarly, the 100 vaccine dose consists of two devices that each deliver 10 mg of dry powder formulation, wherein each 10 mg of dry powder formulation consists of 50 µg of Norwalk VLP, 25 µg MPL® adjuvant, 7 mg chitosan, 1.5 mg mannitol, and 1.5 mg sucrose. The formulation of Adjuvant/Excipient is the same as the Norwalk VLP vaccine except that no Norwalk VLP antigen is included in the formulation. The formulation of the Adjuvant/Excipient (also referred to as dry powder matrix) is summarized in Table 4 in Example 2. The placebo group receives two empty devices.

The volunteers keep a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving either one of two doses of the Norwalk VLP vaccine, dry powder matrix alone, or the placebo. Interim medical histories are obtained at each follow-up visit (days 7±1, 21±2, 28±2, 56±2 and 180±14); volunteers are queried about interim illness, medications, and doctor's visits. Volunteers are asked to report all serious or severe adverse events including events that are not solicited during follow up visits. Volunteers have CBC and serum creatinine, glucose, AST, and ALT assessed on days 7 and 28 (7 days after each immunization) and, if abnormal, the abnormal laboratory test is followed until the test becomes normal or stabilizes.

Blood is collected before immunization and on days 7±1, 21±2, 28±2, 56±2, and 180±14 to measure serum antibodies to the Norwalk VLP vaccine by enzyme-linked immunosorbent assays (ELISA). Before and on day 7 after administration of each dose of vaccine, dry powder matrix alone, or placebo, peripheral blood lymphocytes are collected to detect antibody secreting cells by ELISPOT assay. Before and on days 21±2, 56±2 and 180±14 after vaccination, whole blood is obtained to separate cells and freeze for future studies of cell mediated immunity, including cytokine production in response to Norwalk VLP antigen, and lymphoproliferation. Whole stool samples are collected before immunization and on days 7±1, 21±2, 28±2, 56±2, and day 180±14 for anti-Norwalk VLP sIgA screening. Saliva is collected with a commercially available device (Salivette, Sarstedt, Newton, N.C.) before immunization and on days 7±1, 21±2, 28±2, 56±2, and if positive for mucosal antibodies at day 56, a day 180±14 sample is collected and screened for anti-Norwalk VLP sIgA. Blood is also screened for memory B-cells on days 0, 21, 56 and 180.

Methods used to analyze the blood, stool, and saliva samples collected from immunized individuals, or individuals receiving the dry powder matrix alone or placebo are described in detail in Example 2.

Example 4. Norwalk Virus Challenge Study in Humans Immunized with Norwalk Virus VLP Vaccine Formulation A multi-site, randomized, double-blind, placebo-controlled Phase 1-2 challenge study is conducted in 80 human volunteers immunized with the Norwalk VLP vaccine described in Example 2 above. Eligible subjects include those 18-50 years of age, in good health, who express the H type-1 oligosaccharide (as measured by positive salivary secretor status) and who are other than Type B or AB blood type. Subjects who are non H type-1 secretors or who have Type B or AB blood are reported to be more resistant to infection with Norwalk virus and are excluded from the study. At least 80% of volunteers are expected to be eligible based on these two criteria.

Following screening, eligible volunteers who meet all acceptance criteria are randomized (1:1) into one of two equal sized cohorts with approximately 40 volunteers in each cohort. Cohort 1 is immunized with Norwalk VLP and cohort 2 receives placebo. Volunteers are immunized with 10 mg Norwalk VLP vaccine in each nostril (20 mg total dry powder) or placebo. Each 10 mg of Norwalk VLP vaccine contains 50 μg of Norwalk VLP, 7 mg chitosan, 25 μg MPL®, 1.5 mg of sucrose and approximately 1.5 mg of mannitol. Thus, each volunteer in cohort 1 receives a total dosage of 100 μg of Norwalk VLP antigen at each immunization. Volunteers receive vaccine or placebo on study days 0 and 21.

The safety of the Norwalk virus VLP vaccine compared to placebo is assessed. Volunteers keep a diary for 7 days following each immunization with the vaccine or placebo to document the severity and duration of adverse events. Serious adverse events (SAEs) and the occurrence of any significant new medical conditions is followed for 6 months after the last dose of vaccine or placebo and for 4 months after the challenge with infectious virus.

All volunteers are challenged with infectious Norwalk virus between 21 to 42 days after the second dose of vaccine or placebo (between study days 42 and 56). Each volunteer receives at or > than the 50% Human Infectious Dose (HID 50), i.e. the amount of infectious virus that is expected to cause disease in at least 50% of volunteers in the placebo group. The HID 50 is between about 48 and about 480 viral equivalents of the Norwalk virus. The Norwalk virus is mixed with sterile water and given orally. The inoculation is preceded by ingestion of 500 mg sodium bicarbonate in water, to prevent breakdown of the virus by stomach acid and pepsin. A second ingestion of sodium bicarbonate solution (500 mg sodium bicarbonate in water) is taken 5 minutes after oral inoculation of the infectious virus. The volunteers remain at the challenge facility for at least 4 days and at least 18 hours after symptoms/signs of acute gastroenteritis (vomiting, diarrhea, loose stool, abdominal pain, nausea, and fever) are absent.

Several metrics are monitored to determine the efficacy of the Norwalk VLP vaccine in preventing or reducing symptoms/signs of acute gastroenteritis induced by the viral challenge. All volunteers record their clinical symptoms of acute gastroenteritis and these symptoms are documented by the research staff at the study sites. Disease symptoms/signs from cohort 1 receiving the vaccine are compared to cohort 2 placebo recipients.

Sera and stool samples are routinely collected from all volunteers prior to immunization with the vaccine or placebo, and after challenge. Serum samples are analyzed by ELISA for IgA and IgG, titers against the Norwalk VLPs. The Norwalk antigen and Norwalk RNA are tested in stool samples by ELISA and PCR, respectively, which indicate the presence of virus, the amount of virus shed from the intestines, and the duration of viral shedding. Subjects who become ill after challenge, are subject to additional laboratory studies including serum chemistries, BUN, creatinine, and liver function tests until symptoms/signs resolve.

Results from the vaccine group (cohort 1) and the placebo group (cohort 2) are compared to assess the protective efficacy of the vaccine against Norovirus disease overall (primary endpoint), and/or its efficacy in ameliorating the symptoms/signs (severity and # of days of illness) and/or the reduction of the presence, the amount and/or the duration of virus shedding (secondary endpoints).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

REFERENCES

1. Glass, R I, J S Noel, T Ando, R L Fankhauser, G Belloit, A Mounts, U D Parasher, J S Bresee and S S Monroe. The Epidemiology of Enteric Caliciviruses from Human: A Reassessment Using New Diagnostics. *J Infect Dis* 2000; 181 (Sup 2): S254-S261.
2. Hardy, M E. Norwalk and "Norwalk-like Viruses" in Epidemic Gastroenteritis. *Clin Lab Med* 1999; 19(3): 675-90.
3. Jiang, X, D Y Graham, K N Wang, and M K Estes. Noralk Virus Genome Cloning and Characterization. *Science* 1990; 250: 1580-1583.
4. Jiang, X, M Want, D Y Graham, and M K Estes. Expression, Self-Assembly, and Antigenicity of the Norwalk Virus Capsid Protein. *J Virol* 1992; 66: 6527-6532.
5. Glass, P, L J White, J M Ball, I Leparc-Goffart, M E Hardy, and M K Estes. Norwalk Virus Open Reading Frame 3 Encodes a Minor Structural Protein. *J Virol* 2000; 74: 6581-6591.

6. Lindesmith, L, C Moe, S Marionneau, N Ruvoen, X Jiang, L Lindblad, P Stewart, J LePendu, and R Baric. Human Susceptiblity and Resistance to Norwalk Virus Infection. *Nat Med* 2003; 9: 548-553.
7. Parrino, T A, D S Schreiber, J S Trier, A Z Kapikian, and N R Blacklow. Clinical Immunity in Acute Gastroenteritis Caused by Norwalk Agent. *N Engl J Med* 1977; 297: 86-89.
8. Wyatt, R G, R Dolin, N R Blacklow, H L DuPont, R F Buscho, T S Thornhill, A Z Kapikian, and R M Chanock. Comparison of Three Agents of Acute Infectious Nonbacterial Gastroenteritis by Cross-challenge in Volunteers. *J Infect Dis* 1974; 129: 709.
9. Ball, J M, D Y Graham, A R Opekum, M A Gilger, R A Guerrero, and M K Estes. Recombinant Norwalk Viruslike Particles Given Orally to Volunteers: Phase I Study. *Gastroenterology* 1999; 117: 40-48.
10. Tacket, C O, MB Sztein, G A Losonky, S S Wasserman, and M K Estes. Humoral, Mucosal, and Cellular Immune Responses to Oral Nowalk Virus-like Particles in Volunteers. *Clin Immunol* 2003; 108: 241.
11. Guerrero, R A, J M Ball, S S Krater, S E Pacheco, J D Clements, and M K Estes. Recombinant Norwalk Viruslike Particles Administered Intranasally to Mice Induce Systemic and Mucosal (Fecal and Vaginal) Immune Responses. *J Virol* 2001; 75: 9713.
12. Nicollier-Jamot, B, A Ogier, L Piroth, P Pothier, and E Kohli. Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. *Vaccine* 2004; 22:1079-1086.
13. Periwal, S B, K R Kourie, N Ramachandaran, S J Blakeney, S DeBruin, D Zhu, T J Zamb, L Smith, S Udem, J H Eldridge, K E Shroff, and P A Reilly. A Modified Cholera Holotoxin CT-E29H Enhances Systemic and Mucosal Immune Responses to Recombinant Norwalk Virus-like Particle Vaccine. *Vaccine* 2003; 21: 376-385.
14. Isaka, M, Y Yasuda, S Kozuka, T Taniguchi, K Matano, J Maeyama, T Komiya, K Ohkuma, N Goto, and K Tochikubo. Induction of systemic and mucosal antibody responses in mice immunized intranasally with aluminium-non-adsorbed diphtheria toxoid together with recombinant cholera toxin B subunit as an adjuvant. *Vaccine* 1999; 18: 743-751.
15. Kozlowski, P A, S Cu-Uvin, M R Neutra, and T P Flanigan. Comparison of the oral, rectal, and vaginal immunization routes for induction of antibodies in rectal and genital tract secretions of women. *Infect Immun* 1997; 65: 1387-1394.
16. Mestecky, J, S M Michalek, Z Moldoveanu, and M W Russell. Routes of immunization and antigen delivery systems for optimal mucosal immune responses in humans. *Behring Inst Mitt* 1997; 33-43.
17. Wu, H Y, and M W Russell. Nasal lymphoid tissue, intranasal immunization, and compartmentalization of the common mucosal immune system. *Immunol Res* 1997; 16: 187-201.
18. Evans, J T, C W Cluff, D A Johnson, M J Lacy, D H Persing, and J R Baldridge. Enhancement of antigen-specific immunity via the TLR4 ligands MPL adjuvant and Ribi 529. *Expert Rev Vaccines* 2003; 2: 219-229.
19. Baldridge, J R, Y Yorgensen, J R Ward, and J T Ulrich. Monophosphoryl lipid A enhances mucosal and systemic immunity to vaccine antigens following intranasal administration [In Process Citation]. *Vaccine* 2000; 18: 2416-2425.
20. Yang, Q B, M Martin, S M Michalek, and J Katz. Mechanisms of monophosphoryl lipid A augmentation of host responses to recombinant HagB from *Porphyromonas gingivalis*. *Infect Immun* 2002; 70: 3557-3565.
21. Baldrick, P, D Richardson, G Elliott, and AW Wheeler. Safety evaluation of monophosphoryl lipid A (MPL): an immunostimulatory adjuvant. *Regul Toxicol Pharmacol* 2002; 35: 398-413.
22. Baldridge, J R, P McGowan, JT Evans, C Cluff, S Mossman, D Johnson, and D Persing. Taking a toll on human disease: Toll-like receptor 4 agonists as vaccine adjuvants and monotherapeutic agents. *Expert Opin Biol Ther* 2004; 4: 1129-1138.
23. Persing, D H, R N Coler, M J Lacy, D A Johnson, J R Baldridge, R M Hershberg, and S G Reed. Taking toll: lipid A mimetics as adjuvants and immunomodulators. *Trends Microbiol* 2002; 10: S32-37.
24. Illum, L. Nasal drug delivery—possibilities, problems and solutions. *J Control Release* 2003; 87: 187-198.
25. Illum, L, I Jabbal-Gill, M Hinchcliffe, A N Fisher, and S S Davis. Chitosan as a novel nasal delivery system for vaccines. *Adv Drug Deliv Rev* 2001; 51: 81-96.
26. Davis, S S. Delivery of peptide and non-peptide drugs through the respiratory tract. *Pharm Sci Technol Today* 1999; 2: 450-456.
27. Bacon, A, J Makin, P J Sizer, I Jabbal-Gill, M Hinchcliffe, L Illum, S Chatfield, and M Roberts. Carbohydrate biopolymers enhance antibody responses to mucosally delivered vaccine antigens. *Infect Immun* 2000; 68: 5764-5770.
28. van der Lubben, I M, JC Verhoef, G Borchard, and H E Junginger. Chitosan for mucosal vaccination. *Adv Drug Deliv Rev* 2001; 52: 139-144.
29. van der Lubben, I M, J C Verhoef, G Borchard, and H E Junginger. Chitosan and its derivatives in mucosal drug and vaccine delivery. *Eur J Pharm Sci* 2001; 14: 201-207.
30. Lim, S T, B Forbes, G P Martin, and M B Brown. In vivo and in vitro characterization of novel microparticulates based on hyaluronan and chitosan hydroglutamate. *AAPS Pharm Sci Tech* 2001; 2: 20.
31. Jabbal-Gill, I, AN Fisher, R Rappuoli, S S Davis, and L Illum. Stimulation of mucosal and systemic antibody responses against *Bordetella pertussis* filamentous hemagglutinin and recombinant pertussis toxin after nasal administration with chitosan in mice. Vaccine 1998; 16: 2039-2046.
32. Mills, K H, C Cosgrove, E A McNeela, A Sexton, R Giemza, I Jabbal-Gill, A Church, W Lin, L Illum, A Podda, R Rappuoli, M Pizza, G E Griffin, and D J Lewis. Protective levels of diphtheria-neutralizing antibody induced in healthy volunteers by unilateral priming-boosting intranasal immunization associated with restricted ipsilateral mucosal secretory immunoglobulin. *A Infect Immun* 2003; 71: 726-732.
33. McNeela, E A., I Jabbal-Gill, L Illum, M Pizza, R Rappuoli, A Podda, D J Lewis, and K H Mills. Intranasal immunization with genetically detoxified diphtheria toxin induces T cell responses in humans: enhancement of Th2 responses and toxin-neutralizing antibodies by formulation with chitosan. *Vaccine* 2004; 22: 909-914.
34. Mikszta, J A., V J Sullivan, C Dean, A M Waterston, J B Alarcon, J P Dekker, 3rd, J M Brittingham, J Huang, C R Hwang, M Ferriter, G Jiang, K Mar, K U Saikh, B G Stiles, C J Roy, R G Ulrich, and N G Harvey. Protective immunization against inhalational anthrax: a comparison of minimally invasive delivery platforms. *J Infect Dis* 2005; 191: 278-288.
35. Huang, J, R J Garmise, T M Crowder, K Mar, C R Hwang, A J Hickey, J A Mikszta, and V J Sullivan. A novel dry powder influenza vaccine and intranasal delivery technology: induction of systemic and mucosal immune responses in rats. *Vaccine* 2004; 23: 794-801.
36. GSK Press Room.
37. Corixa Press Room.
38. BioMira Web Site.

What is claimed is:

1. A method of eliciting protective immunity to a Norovirus infection in a human comprising administering to the human a vaccine comprising at least two Norovirus virus-like particles (VLPs), wherein the at least two VLPs represent different Norovirus genotypes, wherein at least one Norovirus VLP is present in the vaccine in a dose amount of from about 1 ug to about 200 ug, and wherein the vaccine is able to elicit immunity against each Norovirus genotype represented in the vaccine.

2. The method of claim 1, wherein each of the at least two Norovirus VLPs are present in the vaccine in a dose amount of from about 1 μg to about 200 μg.

3. The method of claim 1, wherein the genotypes of the Norovirus VLPs represented in the vaccine are selected from the group consisting of Norovirus genogroup I and genogroup II viral strains.

4. The method of claim 1, wherein the Norovirus VLPs are monovalent VLPs.

5. The method of claim 1, wherein the Norovirus VLPs are multivalent VLPs.

6. The method of claim 4, wherein the Norovirus VLPs are monovalent VLPs representing different genogroups.

7. The method of claim 6, wherein the Norovirus VLPs comprise Norwalk virus VLPs and Houston virus VLPs.

8. The method of claim 1, wherein the vaccine further comprises an adjuvant that is not a bacterially-derived exotoxin.

9. The method of claim 8, wherein the adjuvant is selected from the group consisting of toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly (lactide-co-glycolides) (PLG) microparticles, poloxamer particles, microparticles, and liposomes.

10. The method of claim 9, wherein the adjuvant is a toll-like receptor (TLR) agonist.

11. The method of claim 9, wherein the adjuvant is MPL.

12. The method of claim 9, wherein the adjuvant is aluminum hydroxide.

13. The method of claim 9, wherein the adjuvant comprises MPL and aluminum hydroxide.

14. The method of claim 1, wherein the vaccine is in a powder formulation.

15. The method of claim 1, wherein the vaccine is in a liquid formulation.

16. The method of claim 1, wherein the vaccine is administered to the human by a route selected from the group consisting of mucosal, intranasal, intramuscular, intravenous, subcutaneous, intradermal, subdermal, and transdermal routes of administration.

17. The method of claim 16, wherein the vaccine is administered intranasally.

18. The method of claim 17, wherein the vaccine is administered to one or both nostrils.

19. The method of claim 16, wherein the vaccine is administered intramuscularly.

20. The method of claim 1, wherein the vaccine confers protection from one or more symptoms of Norovirus infection.

* * * * *